United States Patent
Lipshutz et al.

(10) Patent No.: US 12,281,323 B2
(45) Date of Patent: Apr. 22, 2025

(54) TREATMENT FOR RESTORING UREAGENESIS IN CARBAMOYL PHOSPHATE SYNTHETASE 1 DEFICIENCY

(71) Applicant: The Regents of the University of California, Oakland, CA (US)

(72) Inventors: Gerald Lipshutz, Los Angeles, CA (US); Matthew Nitzahn, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 818 days.

(21) Appl. No.: 17/601,557

(22) PCT Filed: Apr. 15, 2020

(86) PCT No.: PCT/US2020/028303
§ 371 (c)(1),
(2) Date: Oct. 5, 2021

(87) PCT Pub. No.: WO2020/214694
PCT Pub. Date: Oct. 22, 2020

(65) Prior Publication Data
US 2022/0162639 A1    May 26, 2022

Related U.S. Application Data

(60) Provisional application No. 62/833,853, filed on Apr. 15, 2019.

(51) Int. Cl.
*C12N 15/86* (2006.01)
*C12N 9/00* (2006.01)

(52) U.S. Cl.
CPC .............. *C12N 15/86* (2013.01); *C12N 9/93* (2013.01); *C12N 2750/14143* (2013.01); *C12N 2750/14144* (2013.01); *C12N 2800/22* (2013.01); *C12Y 603/04016* (2013.01)

(58) Field of Classification Search
None
See application file for complete search history.

(56) References Cited

U.S. PATENT DOCUMENTS

| | | | |
|---|---|---|---|
| 8,999,380 B2 * | 4/2015 | Bancel | A61P 17/00 530/358 |
| 2012/0137379 A1 | 5/2012 | Gao et al. | |
| 2013/0259924 A1 | 10/2013 | Bancel et al. | |
| 2014/0155468 A1 | 6/2014 | Gregory et al. | |

OTHER PUBLICATIONS

Khoja et al. Conditional disruption of hepatic carbamoyl phosphate synthetase 1 in mice results in hyperammonemia without orotic aciduria and can be corrected by liver-directed gene therapy. Molecular Genetics and Metabolism, vol. 124, Issue 4, Aug. 2018, pp. 243-253.*

Duan et al. Expanding AAV Packaging Capacity with Trans-splicing or Overlapping Vectors: A Quantitative Comparison. Molecular Therapy, 2001, 4: 385-391.*

PCT International Search Report & Written Opinion dated Sep. 23, 2020 for PCT Application No. PCT/US20/28303.

Khoja, S., et al., "Conditional Disruption of Hepatic Carbamoyl Phosphate Synthetase 1 in Mice Results in Hyperammonemia without Orotic Aciduria and Can be Corrected by Liver-Directed Gene Therapy", Molecular Genetics and Metabolism, Aug. 2018, pp. 1-26, vol. 124, No. 4.

National Center for Biotechnology Information, Predicted: Latimeria chalumnae carbamoyl-phosphate synthetase 2, aspartate transcarbamylase, and dihydroorotase (CAD), mRNA, Genbank entry (online). National Institute of Biotechnology Information, Oct. 26, 2015 (Retrieved on Jul. 20, 2020), https://www.ncbi.nlm.nih.gOv/nucleotide/XM_014490371.1>, pp. 1-3.

Adam, A.A.A., et al., "Overexpression of carbamoyl-phosphate synthase 1 significantly improves ureagenesis of human liver HepaRG cells only when cultured under shaking conditions", Mitochondrion, Jul. 2019, pp. 1-14, vol. 47.

Zhang, Y., et al., "Cell and Gene Therapy for Carbamoyl Phosphate Synthetase 1 Deficiency", Journal of Pediatrics & Neonatal Care, Jul. 14, 2017, pp. 1-5, vol. 7, No. 1.

* cited by examiner

*Primary Examiner* — Nianxiang Zou
(74) *Attorney, Agent, or Firm* — GATES & COOPER LLP

(57) ABSTRACT

Carbamoyl phosphate synthetase 1 (CPS1) deficiency is a metabolic disorder of the liver that results m abnormal nitrogen metabolism. To illustrate the ability of gene therapy to treat CPS1 deficiency, two adeno-associated viruses encoding portions of a codon optimized CPS1 were generated and tested in a conditional CPS1 knock out mouse model. When administered to mice having knocked out endogenous CPS1 expression, mice from this model demonstrate homologous recombination and reconstitution of the codon optimized CPS1 gene, expression of the CPS1 protein and the associated control of plasma ammonia following the administered AAVs comprising the CPS1 gene sequences. While all control mice perish, the mice in this model live and have normal behavior. As there is no effective therapy for human patients with the CPS1 disorder, this invention can address this unmet need for these patients.

11 Claims, 6 Drawing Sheets
Specification includes a Sequence Listing.

Split AAV Concatemerization

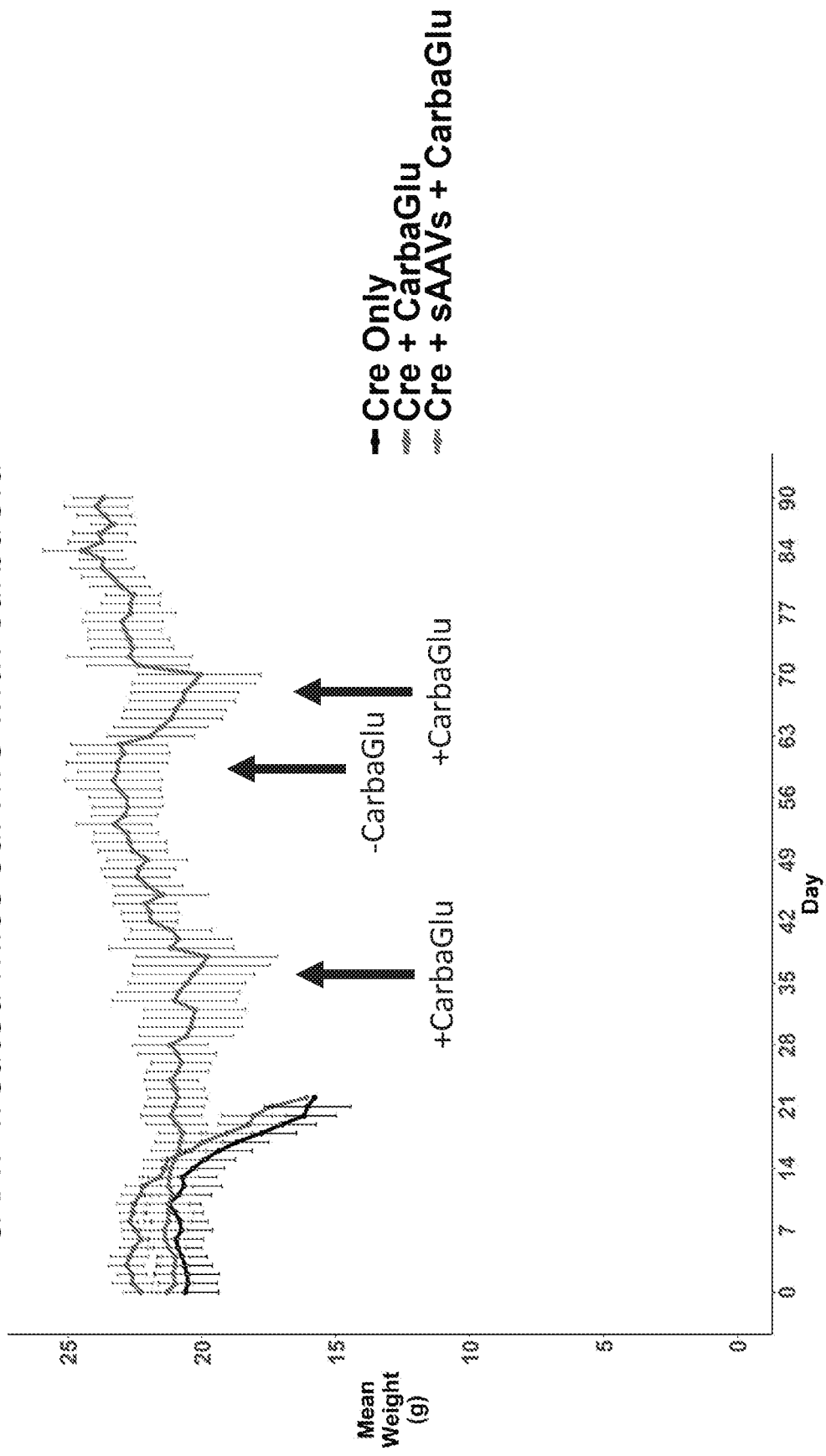

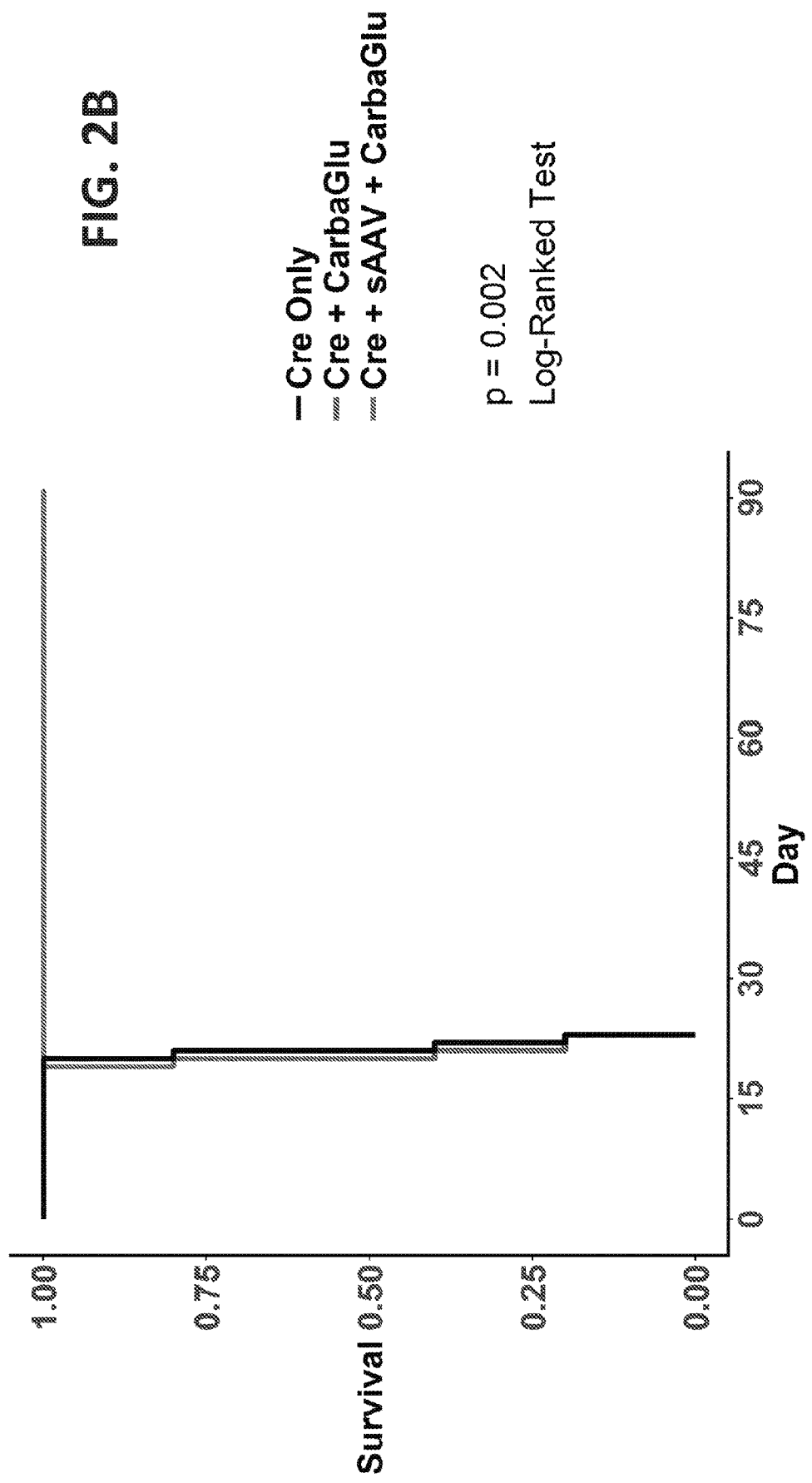

SEQUENCE LISTING

```
<160> NUMBER OF SEQ ID NOS: 11

<210> SEQ ID NO 1
<211> LENGTH: 1500
<212> TYPE: PRT
<213> ORGANISM: Homo sapiens

<400> SEQUENCE: 1

Met Thr Arg Ile Leu Thr Ala Phe Lys Val Val Arg Thr Leu Lys Thr
1               5                   10                  15

Gly Phe Gly Phe Thr Asn Val Thr Ala His Gln Lys Trp Lys Phe Ser
            20                  25                  30

Arg Pro Gly Ile Arg Leu Leu Ser Val Lys Ala Gln Thr Ala His Ile
        35                  40                  45

Val Leu Glu Asp Gly Thr Lys Met Lys Gly Tyr Ser Phe Gly His Pro
    50                  55                  60

Ser Ser Val Ala Gly Glu Val Val Phe Asn Thr Gly Leu Gly Gly Tyr
65                  70                  75                  80

Pro Glu Ala Ile Thr Asp Pro Ala Tyr Lys Gly Gln Ile Leu Thr Met
                85                  90                  95

Ala Asn Pro Ile Ile Gly Asn Gly Gly Ala Pro Asp Thr Thr Ala Leu
            100                 105                 110

Asp Glu Leu Gly Leu Ser Lys Tyr Leu Glu Ser Asn Gly Ile Lys Val
        115                 120                 125

Ser Gly Leu Leu Val Leu Asp Tyr Ser Lys Asp Tyr Asn His Trp Leu
    130                 135                 140

Ala Thr Lys Ser Leu Gly Gln Trp Leu Gln Glu Glu Lys Val Pro Ala
145                 150                 155                 160

Ile Tyr Gly Val Asp Thr Arg Met Leu Thr Lys Ile Ile Arg Asp Lys
                165                 170                 175

Gly Thr Met Leu Gly Lys Ile Glu Phe Glu Gly Gln Pro Val Asp Phe
            180                 185                 190

Val Asp Pro Asn Lys Gln Asn Leu Ile Ala Glu Val Ser Thr Lys Asp
        195                 200                 205

Val Lys Val Tyr Gly Lys Gly Asn Pro Thr Lys Val Val Ala Val Asp
    210                 215                 220

Cys Gly Ile Lys Asn Asn Val Ile Arg Leu Leu Val Lys Arg Gly Ala
225                 230                 235                 240

Glu Val His Leu Val Pro Trp Asn His Asp Phe Thr Lys Met Glu Tyr
                245                 250                 255
```

```
Asp Gly Ile Leu Ile Ala Gly Gly Pro Gly Asn Pro Ala Leu Ala Glu
            260                 265                 270

Pro Leu Ile Gln Asn Val Arg Lys Ile Leu Glu Ser Asp Arg Lys Glu
275                 280                 285

Pro Leu Phe Gly Ile Ser Thr Gly Asn Leu Ile Thr Gly Leu Ala Ala
        290                 295                 300

Gly Ala Lys Thr Tyr Lys Met Ser Met Ala Asn Arg Gly Gln Asn Gln
305                 310                 315                 320

Pro Val Leu Asn Ile Thr Asn Lys Gln Ala Phe Ile Thr Ala Gln Asn
                325                 330                 335

His Gly Tyr Ala Leu Asp Asn Thr Leu Pro Ala Gly Trp Lys Pro Leu
            340                 345                 350

Phe Val Asn Val Asn Asp Gln Thr Asn Glu Gly Ile Met His Glu Ser
                355                 360                 365

Lys Pro Phe Phe Ala Val Gln Phe His Pro Glu Val Thr Pro Gly Pro
    370                 375                 380

Ile Asp Thr Glu Tyr Leu Phe Asp Ser Phe Ser Leu Ile Lys Lys
385                 390                 395                 400

Gly Lys Ala Thr Thr Ile Thr Ser Val Leu Pro Lys Pro Ala Leu Val
                405                 410                 415

Ala Ser Arg Val Glu Val Ser Lys Val Leu Ile Leu Gly Ser Gly Gly
            420                 425                 430

Leu Ser Ile Gly Gln Ala Gly Glu Phe Asp Tyr Ser Gly Ser Gln Ala
        435                 440                 445

Val Lys Ala Met Lys Glu Glu Asn Val Lys Thr Val Leu Met Asn Pro
450                 455                 460

Asn Ile Ala Ser Val Gln Thr Asn Glu Val Gly Leu Lys Gln Ala Asp
465                 470                 475                 480

Thr Val Tyr Phe Leu Pro Ile Thr Pro Gln Phe Val Thr Glu Val Ile
                485                 490                 495

Lys Ala Glu Gln Pro Asp Gly Leu Ile Leu Gly Met Gly Gly Gln Thr
            500                 505                 510

Ala Leu Asn Cys Gly Val Glu Leu Phe Lys Arg Gly Val Leu Lys Glu
        515                 520                 525

Tyr Gly Val Lys Val Leu Gly Thr Ser Val Glu Ser Ile Met Ala Thr
    530                 535                 540

Glu Asp Arg Gln Leu Phe Ser Asp Lys Leu Asn Glu Ile Asn Glu Lys
545                 550                 555                 560

Ile Ala Pro Ser Phe Ala Val Glu Ser Ile Glu Asp Ala Leu Lys Ala
                565                 570                 575

Ala Asp Thr Ile Gly Tyr Pro Val Met Ile Arg Ser Ala Tyr Ala Leu
            580                 585                 590

Gly Gly Leu Gly Ser Gly Ile Cys Pro Asn Arg Glu Thr Leu Met Asp
        595                 600                 605

Leu Ser Thr Lys Ala Phe Ala Met Thr Asn Gln Ile Leu Val Glu Lys
    610                 615                 620

Ser Val Thr Gly Trp Lys Glu Ile Glu Tyr Glu Val Val Arg Asp Ala
625                 630                 635                 640

Asp Asp Asn Cys Val Thr Val Cys Asn Met Glu Asn Val Asp Ala Met
                645                 650                 655

Gly Val His Thr Gly Asp Ser Val Val Val Ala Pro Ala Gln Thr Leu
            660                 665                 670

Ser Asn Ala Glu Phe Gln Met Leu Arg Arg Thr Ser Ile Asn Val Val
```

```
                675                 680                 685
Arg His Leu Gly Ile Val Gly Glu Cys Asn Ile Gln Phe Ala Leu His
    690                 695                 700
Pro Thr Ser Met Glu Tyr Cys Ile Ile Glu Val Asn Ala Arg Leu Ser
705                 710                 715                 720
Arg Ser Ser Ala Leu Ala Ser Lys Ala Thr Gly Tyr Pro Leu Ala Phe
            725                 730                 735
Ile Ala Ala Lys Ile Ala Leu Gly Ile Pro Leu Pro Glu Ile Lys Asn
            740                 745                 750
Val Val Ser Gly Lys Thr Ser Ala Cys Phe Glu Pro Ser Leu Asp Tyr
        755                 760                 765
Met Val Thr Lys Ile Pro Arg Trp Asp Leu Asp Arg Phe His Gly Thr
770                 775                 780
Ser Ser Arg Ile Gly Ser Ser Met Lys Ser Val Gly Glu Val Met Ala
785                 790                 795                 800
Ile Gly Arg Thr Phe Glu Glu Ser Phe Gln Lys Ala Leu Arg Met Cys
                805                 810                 815
His Pro Ser Ile Glu Gly Phe Thr Pro Arg Leu Pro Met Asn Lys Glu
            820                 825                 830
Trp Pro Ser Asn Leu Asp Leu Arg Lys Glu Leu Ser Glu Pro Ser Ser
            835                 840                 845
Thr Arg Ile Tyr Ala Ile Ala Lys Ala Ile Asp Asp Asn Met Ser Leu
    850                 855                 860
Asp Glu Ile Glu Lys Leu Thr Tyr Ile Asp Lys Trp Phe Leu Tyr Lys
865                 870                 875                 880
Met Arg Asp Ile Leu Asn Met Glu Lys Thr Leu Lys Gly Leu Asn Ser
                885                 890                 895
Glu Ser Met Thr Glu Glu Thr Leu Lys Arg Ala Lys Glu Ile Gly Phe
            900                 905                 910
Ser Asp Lys Gln Ile Ser Lys Cys Leu Gly Leu Thr Glu Ala Gln Thr
            915                 920                 925
Arg Glu Leu Arg Leu Lys Lys Asn Ile His Pro Trp Val Lys Gln Ile
    930                 935                 940
Asp Thr Leu Ala Ala Glu Tyr Pro Ser Val Thr Asn Tyr Leu Tyr Val
945                 950                 955                 960
Thr Tyr Asn Gly Gln Glu His Asp Val Asn Phe Asp Asp His Gly Met
                965                 970                 975
Met Val Leu Gly Cys Gly Pro Tyr His Ile Gly Ser Ser Val Glu Phe
            980                 985                 990
Asp Trp Cys Ala Val Ser Ser Ile Arg Thr Leu Arg Gln Leu Gly Lys
    995                 1000                1005
Lys Thr Val Val Val Asn Cys Asn Pro Glu Thr Val Ser Thr Asp
    1010                1015                1020
Phe Asp Glu Cys Asp Lys Leu Tyr Phe Glu Glu Leu Ser Leu Glu
    1025                1030                1035
Arg Ile Leu Asp Ile Tyr His Gln Glu Ala Cys Gly Gly Cys Ile
    1040                1045                1050
Ile Ser Val Gly Gly Gln Ile Pro Asn Asn Leu Ala Val Pro Leu
    1055                1060                1065
Tyr Lys Asn Gly Val Lys Ile Met Gly Thr Ser Pro Leu Gln Ile
    1070                1075                1080
Asp Arg Ala Glu Asp Arg Ser Ile Phe Ser Ala Val Leu Asp Glu
    1085                1090                1095
```

```
Leu Lys Val Ala Gln Ala Pro Trp Lys Ala Val Asn Thr Leu Asn
    1100            1105                1110

Glu Ala Leu Glu Phe Ala Lys Ser Val Asp Tyr Pro Cys Leu Leu
    1115            1120                1125

Arg Pro Ser Tyr Val Leu Ser Gly Ser Ala Met Asn Val Val Phe
    1130            1135                1140

Ser Glu Asp Glu Met Lys Lys Phe Leu Glu Ala Thr Arg Val
    1145            1150                1155

Ser Gln Glu His Pro Val Val Leu Thr Lys Phe Val Glu Gly Ala
    1160            1165                1170

Arg Glu Val Glu Met Asp Ala Val Gly Lys Asp Gly Arg Val Ile
    1175            1180                1185

Ser His Ala Ile Ser Glu His Val Glu Asp Ala Gly Val His Ser
    1190            1195                1200

Gly Asp Ala Thr Leu Met Leu Pro Thr Gln Thr Ile Ser Gln Gly
    1205            1210                1215

Ala Ile Glu Lys Val Lys Asp Ala Thr Arg Lys Ile Ala Lys Ala
    1220            1225                1230

Phe Ala Ile Ser Gly Pro Phe Asn Val Gln Phe Leu Val Lys Gly
    1235            1240                1245

Asn Asp Val Leu Val Ile Glu Cys Asn Leu Arg Ala Ser Arg Ser
    1250            1255                1260

Phe Pro Phe Val Ser Lys Thr Leu Gly Val Asp Phe Ile Asp Val
    1265            1270                1275

Ala Thr Lys Val Met Ile Gly Glu Asn Val Asp Glu Lys His Leu
    1280            1285                1290

Pro Thr Leu Asp His Pro Ile Ile Pro Ala Asp Tyr Val Ala Ile
    1295            1300                1305

Lys Ala Pro Met Phe Ser Trp Pro Arg Leu Arg Asp Ala Asp Pro
    1310            1315                1320

Ile Leu Arg Cys Glu Met Ala Ser Thr Gly Glu Val Ala Cys Phe
    1325            1330                1335

Gly Glu Gly Ile His Thr Ala Phe Leu Lys Ala Met Leu Ser Thr
    1340            1345                1350

Gly Phe Lys Ile Pro Gln Lys Gly Ile Leu Ile Gly Ile Gln Gln
    1355            1360                1365

Ser Phe Arg Pro Arg Phe Leu Gly Val Ala Glu Gln Leu His Asn
    1370            1375                1380

Glu Gly Phe Lys Leu Phe Ala Thr Glu Ala Thr Ser Asp Trp Leu
    1385            1390                1395

Asn Ala Asn Asn Val Pro Ala Thr Pro Val Ala Trp Pro Ser Gln
    1400            1405                1410

Glu Gly Gln Asn Pro Ser Leu Ser Ser Ile Arg Lys Leu Ile Arg
    1415            1420                1425

Asp Gly Ser Ile Asp Leu Val Ile Asn Leu Pro Asn Asn Asn Thr
    1430            1435                1440

Lys Phe Val His Asp Asn Tyr Val Ile Arg Arg Thr Ala Val Asp
    1445            1450                1455

Ser Gly Ile Pro Leu Leu Thr Asn Phe Gln Val Thr Lys Leu Phe
    1460            1465                1470

Ala Glu Ala Val Gln Lys Ser Arg Lys Val Asp Ser Lys Ser Leu
    1475            1480                1485
```

Phe His Tyr Arg Gln Tyr Ser Ala Gly Lys Ala Ala
    1490                1495                1500

<210> SEQ ID NO 2
<211> LENGTH: 4521
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | | | | | |
|---|---|---|---|---|---|
| atgcctcaga | tcataaagat | gacccggatt | cttaccgcat | tcaaggttgt | aaggacccttt 60 |
| aaaaccggct | tcggctttac | taacgtgacc | gcacaccaaa | agtggaagtt | tagcaggccc 120 |
| ggaattcgcc | tccttagtgt | gaaagcccag | accgctcata | tagtccttga | agacggcaca 180 |
| aaaatgaaag | ggtactcatt | cggccatcca | tcatctgtag | ccggtgaggt | cgtgttcaat 240 |
| actggattgg | ggggttatcc | cgaggccata | acagacccag | cttataaggg | ccagatcctg 300 |
| accatggcca | acccaatcat | cgggaacgga | ggtgcgccgg | atacaactgc | gttggatgag 360 |
| ctgggactgt | ccaagtactt | ggagagcaat | ggaattaaag | tttctggact | gctggtactg 420 |
| gactactcaa | aggactacaa | tcattggctg | gccaccaaaa | gtctggggca | atggctgcag 480 |
| gaggagaagg | tgccagctat | atacggagtt | gacactagaa | tgcttaccaa | aattataaga 540 |
| gacaaaggta | ctatgctggg | aaaaattgag | tttgaaggac | agcccgtgga | tttcgtagac 600 |
| cctaataagc | agaatcttat | cgccgaggtg | agcacaaagg | acgttaaggt | ctacggaaaa 660 |
| ggaaatccaa | ctaaggtggt | ggctgttgat | tgtggcatta | agaacaacgt | gatcagactg 720 |
| ctggtgaaac | gcggagctga | agtccatctt | gtcccatgga | atcatgattt | tacgaaaatg 780 |
| gagtatgatg | gaattctcat | cgccggcgga | ccagggaacc | cagccttggc | tgaaccccttt 840 |
| atccaaaacg | ttagaaaaat | actcgaatct | gataggaaag | agccccttttt | tggtatatcc 900 |
| accgaaaact | tgattacagg | ccttgctgca | ggggccaaga | catataagat | gagcatggca 960 |
| aaccgcggac | agaatcagcc | cgtactgaac | attactaata | gcaggctttt | atcaccgca 1020 |
| cagaatcacg | ttacgctctc | gataatacg | ctccctgccg | gctggaagcc | gctcttcgtt 1080 |
| aacgtaaatg | atcagacaaa | cgagggaata | atgcacgaat | ccaaaccctt | cttcgccgtc 1140 |
| cagttccacc | ctgaagtcac | tccaggcccct | attgacacag | aatatctctt | tgactccttc 1200 |
| tttagcctga | taaaaaaggg | gaaggccacc | accataacgt | ccgtcctgcc | taagccagct 1260 |
| ctcgtggcat | caagagtaga | ggtctccaaa | gtgctcatac | ttggtagcgg | gggactgtca 1320 |
| atcggccaag | caggcgagtt | cgattactcc | ggaagccaag | cagttaaggc | tatgaaagaa 1380 |
| gagaacgtta | aaactgtgct | gatgaatcca | aatatagcct | ccgtgcagac | caatgaggtg 1440 |
| ggtctcaagc | aagcagatac | tgtttacttt | cttccaatta | cccccccaatt | cgtaaccgaa 1500 |
| gtcattaagg | ccgagcagcc | tgatggattg | atcctgggta | tgggcggaca | gactgcactg 1560 |
| aattgcggag | tggagttgtt | caaaagggggt | gtgttgaagg | aatatggagt | taaggtactc 1620 |
| ggcacctccg | ttgagagcat | catggcgacc | gaggatagac | agttgttctc | tgataaactg 1680 |
| aacgagatta | tgagaagat | cgcccccctca | ttcgccgtgg | agtctatcga | agatgcactg 1740 |
| aaagccgctg | atacgattgg | ctatcctgta | atgataagaa | gcgcctacgc | cctgggtggc 1800 |
| ctggggtctg | gcatctgccc | taaccgagag | acgctgatgg | acctctccac | aaaagccttc 1860 |
| gccatgacta | accagattct | ggtagaaaaa | tccgtcaccg | gctggaagga | aattgaatac 1920 |
| gaagtagtaa | gagacgctga | tgacaattgc | gtcacagtct | gcaacatgga | aaacgtcgat 1980 |

```
gcgatgggcg tgcacaccgg agattccgtc gttgtggcgc cagcacaaac actctccaat    2040
gctgagttcc agatgctcag aagaacaagc attaacgttg tgcgacatct tgggatagtt    2100
ggcgaatgta acatccaatt tgcactgcac ccaactagca tggaatactg cattatcgaa    2160
gtgaatgcgc ggctgagccg aagcagcgct ctcgccagca aagccacagg ctacccactt    2220
gccttcattg ccgcaaagat tgcactgggc attccactgc ctgagattaa aatgtcgta     2280 agcgggaaga caagcgcctg ttttgaacct tccctggact atatggtgac taagattcct    2340
cggtgggacc ttgataggtt ccatgggacc tcatctagaa taggatcatc aatgaagtct    2400
gtgggtgaag tgatggctat cgggcggacc ttcgaagaga gttttcagaa agcacttcgg    2460
atgtgtcacc cctcaattga gggcttcacc ccccggttgc caatgaacaa ggagtggcca    2520
tcaaacctgg acctgagaaa agagctcagc gagcctagct caactagaat ctacgcaatc    2580
gccaaggcaa tcgacgataa catgtcattg gatgagatag agaagttgac atacatagac    2640
aaatggttcc tctacaaaat gcgagacatt ctgaatatgg agaaaacact gaagggactg    2700
aattctgaga gcatgacgga ggagacactt aagagagcaa aagagattgg gttcagcgat    2760
aagcaaattt caaagtgcct tggactgacc gaagcccaga cacgggagct gagactgaag    2820
aaaaatatac acccatgggt gaagcagatc gacaccctgg cggccgaata tcccagcgtt    2880
actaattacc tgtatgttac atataacggc caagagcatg acgtaaattt tgacgatcat    2940
ggaatgatgg ttttgggatg cggtccctac cacattggct cttcagtgga gtttgattgg    3000
tgcgcagtga gctccattcg gaccctcaga cagcttggaa aaaaacagt ggtggtaaat     3060 tgtaacccgg agactgtgtc aaccgacttc gacgaatgcg acaagttgta ttttgaggaa    3120
ttgagtcttg aaaggattct tgatatctac catcaggaag catgcggagg ctgtattatc    3180
tcagtgggcg ggcagatacc caacaacctt gctgtacctc tctataaaaa cggtgtaaag    3240
atcatgggca cctctcccct ccagattgac agggccgagg accgctcaat tttcagtgct    3300
gtgctggacg aactcaaagt cgctcaagct ccttggaaag ctgttaatac tcttaacgag    3360
gccctcgagt tcgccaagtc tgtgattac ccatgtcttc ttcggccctc ctacgtgctg      3420
tcaggatccg caatgaacgt cgtgttcagc gaggatgaaa tgaagaaatt tctgaggag     3480 gctacacggg tgagtcaaga gcatcctgtg gttttgacta agttcgttga gggcgcccgg    3540
gaagtcgaga tggatgcagt cggtaaagat ggacgggtaa ttagccacgc aattagtgaa    3600
cacgtggaag atgccggggt ccattctggc gacgccactc tcatgctgcc aacacagaca    3660
attagtcagg tgctataga gaaagtgaaa gatgcgacta ggaagatcgc aaaagccttc     3720
gcaatatctg gcccatttaa cgtgcagttt ctcgtgaaag gtaacgacgt cctggtgatc    3780
gagtgtaatc tccgagcgtc acgatccttc cctttcgtaa gcaagaccct cggcgtagac    3840
tttattgacg tggccacgaa agttatgatt ggagagaatg tagacgagaa acacctcccc    3900
actcttgacc atccgatcat ccccgcggat tatgttgcca tcaaggcccc aatgttctct    3960
tggccgcgcc tgcgagacgc tgatcccatc ttgcgctgtg aaatggcaag cacaggcgaa    4020
gtagcatgct tcggcgaagg tattcatacc gcatttctga aggccatgct gagcaccggc    4080
ttcaagatcc cccagaaggg tatcctcatc ggcatccagc agtctttccg cccaagattc    4140
ctgggggtag cagaacaact tcataacgaa ggcttcaagc tgtttgcaac agaagcaacc    4200
tctgattggc tgaacgctaa taatgttcct gcgactccag tcgcctggcc cagccaggaa    4260
ggacaaaatc ccagcctgtc tagcatcaga aaactcatac gagatggctc tatcgacctt    4320
```

| | | | | |
|---|---|---|---|---|
| gttatcaacc | tgcctaataa | caacaccaaa | tttgtccacg | acaactacgt catcagaaga | 4380 |
| actgccgtgg | atagcggtat | ccccctgctg | accaatttcc | aggttaccaa gctctttgca | 4440 |
| gaagctgttc | agaaatctcg | caaggtggat | agcaagtcac | tgtttcacta tcgacaatat | 4500 |
| tcagcgggga | aggctgcata | g | | | 4521 |

<210> SEQ ID NO 3
<211> LENGTH: 467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | | | | | |
|---|---|---|---|---|---|
| gccgtggagt | ctatcgaaga | tgcactgaaa | gccgctgata | cgattggcta tcctgtaatg | 60 |
| ataagaagcg | cctacgccct | gggtggcctg | ggtctggca | tctgccctaa ccgagagacg | 120 |
| ctgatggacc | tctccacaaa | agccttcgcc | atgactaacc | agattctggt agaaaaatcc | 180 |
| gtcaccggct | ggaaggaaat | tgaatacgaa | gtagtaagag | acgctgatga caattgcgtc | 240 |
| acagtctgca | acatggaaaa | cgtcgatgcg | atgggcgtgc | acaccggaga ttccgtcgtt | 300 |
| gtggcgccag | cacaaacact | ctccaatgct | gagttccaga | tgctcagaag aacaagcatt | 360 |
| aacgttgtgc | gacatcttgg | gatagttggc | gaatgtaaca | tccaatttgc actgcaccca | 420 |
| actagcatgg | aatactgcat | tatcgaagtg | aatgcgcggc | tgagccg | 467 |

<210> SEQ ID NO 4
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | | | | | |
|---|---|---|---|---|---|
| gctgcgcgct | cgctcgctca | ctgaggccgc | ccgggcaaag | cccgggcgtc gggcgacctt | 60 |
| tggtcgcccg | gcctcagtga | gcgagcgagc | gcgcagagag | ggagtggcca actccatcac | 120 |
| taggggttcc | ttgtagttaa | tgattaaccc | gccatgctac | ttatctacca gggtaatggg | 180 |

<210> SEQ ID NO 5
<211> LENGTH: 1676
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| | | | | | |
|---|---|---|---|---|---|
| gacattgatt | attgactagt | tattaatagt | aatcaattac | ggggtcatta gttcatagcc | 60 |
| catatatgga | gttccgcgtt | acataactta | cggtaaatgg | cccgcctggc tgaccgccca | 120 |
| acgacccccg | cccattgacg | tcaataatga | cgtatgttcc | catagtaacg ccaataggga | 180 |
| ctttccattg | acgtcaatgg | gtggagtatt | tacggtaaac | tgcccacttg gcagtacatc | 240 |
| aagtgtatca | tatgccaagt | acgcccccta | ttgacgtcaa | tgacggtaaa tggcccgcct | 300 |
| ggcattatgc | ccagtacatg | accttatggg | actttcctac | ttggcagtac atctacgtat | 360 |
| tagtcatcgc | tattaccatg | gtcgaggtga | gccccacgtt | ctgcttcact ctccccatct | 420 |
| ccccccccctc | cccaccccca | attttgtatt | tatttatttt | ttaattattt tgtgcagcga | 480 |

-continued

```
tgggggcggg ggggggggg gggcgcgcgc caggcggggc ggggcggggc gagggcggg      540 gcggggcgag gcggagaggt gcggcggcag ccaatcagag cggcgcgctc cgaaagtttc    600
cttttatggc gaggcggcgg cggcggcggc cctataaaaa gcgaagcgcg cggcgggcgg    660
gagtcgctgc gcgctgcctt cgccccgtgc cccgctccgc cgccgcctcg cgccgcccgc    720
cccggctctg actgaccgcg ttactcccac aggtgagcgg gcgggacggc ccttctcctc    780
cgggctgtaa ttagcgcttg gtttaatgac ggcttgtttc ttttctgtgg ctgcgtgaaa    840
gccttgaggg gctccgggag ggccctttgt gcggggggag cggctcgggg ggtgcgtgcg    900
tgtgtgtgtg cgtggggagc gccgcgtgcg gctccgcgct gcccggcggc tgtgagcgct    960
gcgggcgcgg cgcggggctt tgtgcgctcc gcagtgtgcg cgagggggagc gcggccgggg   1020 gcggtgcccc gcggtgcggg gggggctgcg aggggaacaa aggctgcgtg cggggtgtgt    1080 gcgtggggggg gtgagcaggg ggtgtgggcg cgtcggtcgg gctgcaaccc cccctgcacc   1140
cccctccccg agttgctgag cacggcccgg cttcgggtgc ggggctccgt acggggcgtg    1200
gcgcggggct cgccgtgccg ggcgggggt ggcgcaggt ggggtgccg ggcggggcgg       1260 ggccgcctcg ggccggggag ggctcggggg aggggcgcgg cggccccgg agcgccggcg     1320 gctgtcgagg cgcggcgagc cgcagccatt gccttttatg gtaatcgtgc gagagggcgc    1380
agggacttcc tttgtcccaa atctgtgcgg agccgaaatc tgggaggcgc cgccgcaccc    1440
cctctagcgg gcgcggggcg aagcggtgcg gcgccggcag gaaggaaatg ggcggggagg    1500
gccttcgtgc gtcgccgcgc cgccgtcccc ttctccctct ccagcctcgg ggctgtccgc    1560
ggggggacgg ctgccttcgg gggggacggg gcagggcggg gttcggcttc tggcgtgtga    1620
ccggcggctc tagagcctct gctaaccatg ttcatgcctt cttcttttc ctacag        1676
```

```
<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aataaaggaa atttattttc attgcaatag tgtgttggaa ttttttgtgt ctctca        56

<210> SEQ ID NO 7
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
cccattaccc tggtagataa gtagcatggc gggttaatca ttaactacaa ggaacccta     60 gtgatggagt tggccactcc ctctctgcgc gctcgctcgc tcactgaggc cgggcgacca    120
aaggtcgccc gacgcccggg ctttgcccgg gcggcctcag tgagcgagcg agcgcgcagc    180

<210> SEQ ID NO 8
<211> LENGTH: 7343
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 8
gctgcgcgct cgctcgctca ctgaggccgc ccgggcaaag cccgggcgtc gggcgacctt      60
tggtcgcccg gcctcagtga gcgagcgagc gcgcagagag ggagtggcca actccatcac     120 tagggggttcc ttgtagttaa tgattaaccc gccatgctac ttatctacca gggtaatggg    180
gatcctctag aactatagct agtcgacatt gattattgac tagttattaa tagtaatcaa    240
ttacggggtc attagttcat agcccatata tggagttccg cgttacataa cttacggtaa    300
atggcccgcc tggctgaccg cccaacgacc cccgcccatt gacgtcaata atgacgtatg    360
ttcccatagt aacgccaata gggactttcc attgacgtca atgggtggag tatttacggt    420
aaactgccca cttggcagta catcaagtgt atcatatgcc aagtacgccc cctattgacg    480
tcaatgacgg taaatggccc gcctggcatt atgcccagta catgacctta tgggactttc    540
ctacttggca gtacatctac gtattagtca tcgctattac catggtcgag gtgagcccca    600
cgttctgctt cactctcccc atctccccce cctccccacc cccaattttg tatttattta    660 tttttttaatt attttgtgca gcgatggggg cgggggggggg ggggggcgc gcgccaggcg    720 gggcggggcg gggcgagggg cggggcgggg cgaggcggag aggtgcggcg gcagccaatc    780
agagcggcgc gctccgaaag tttccttttta tggcgaggcg gcggcggcgg cggccctata    840
aaaagcgaag cgcgcggcgg gcgggagtcg ctgcgcgctg ccttcgcccc gtgccccgct    900
ccgccgccgc ctcgcgccgc ccgccccggc tctgactgac cgcgttactc ccacaggtga    960
gcgggcggga cggcccttct cctccgggct gtaattagcg cttggtttaa tgacggcttg   1020
tttcttttct gtggctgcgt gaaagccttg agggccccg ggaggcccct ttgtgcgggg   1080
ggagcggctc gggggtgcg tgcgtgtgtg tgtgcgtggg gagcgccgcg tgcggctccg   1140
cgctgcccgg cggctgtgag cgctgcgggc gcggcgcggg gctttgtgcg ctccgcagtg   1200
tgcgcgaggg gagcgcggcc ggggcggtg ccccgcggtg cggggggggc tgcgagggga   1260
acaaaggctg cgtgcgggt gtgtgcgtgg ggggtgagc aggggggtgtg ggcgcgtcgg   1320 tcgggctgca accccccctg caccccccctc cccgagttgc tgagcacggc ccggcttcgg   1380
gtgcggggct ccgtacgggg cgtggcgcgg ggctcgccgt gccgggcggg gggtggcggc   1440
aggtgggggt gccgggcggg gcggggccgc ctcgggccgg ggagggctcg ggggagggc   1500 gcggcggccc ccggagcgcc ggcggctgtc gaggcgcggc gagccgcagc cattgccttt   1560
tatggtaatc gtgcgagagg gcgcagggac ttcctttgtc ccaaatctgt gcggagccga   1620
aatctgggag gcgccgccgc acccctcta gcgggcgcgg ggcgaagcgg tgcggcgccg   1680
gcaggaagga aatgggcggg gagggccttc gtgcgtcgcc gcgccgccgt cccttctcc    1740 ctctccagcc tcggggctgt ccgcgggggg acggctgcct tcggggggga cggggcaggg   1800
cggggttcgg cttctggcgt gtgaccggcg gctctagagc ctctgctaac catgttcatg   1860
ccttcttctt tttcctacag ctcctgggca acgtgctggt tattgtgctg tctcatcatt   1920
ttggcaaaga attcacgcgt ggtaccacta gtcatatgtt aattaaatgc ctcagatcat   1980
aaagatgacc cggattctta ccgcattcaa ggttgtaagg acccttaaaa ccggcttcgg   2040
ctttactaac gtgaccgcac accaaaagtg gaagtttagc aggcccggaa ttcgcctcct   2100
tagtgtgaaa gcccagaccg ctcatatagt ccttgaagac ggcacaaaaa tgaaagggta   2160
ctcattcggc catccatcat ctgtagccgg tgaggtcgtg ttcaatactg gattggggg    2220 ttatcccgag gccataacag acccagctta taagggccag atcctgacca tggccaaccc   2280
aatcatcggg aacggaggtg cgccggatac aactgcgttg gatgagctgg gactgtccaa   2340
```

```
gtacttggag agcaatggaa ttaaagtttc tggactgctg gtactggact actcaaagga   2400
ctacaatcat tggctggcca ccaaaagtct ggggcaatgg ctgcaggagg agaaggtgcc   2460
agctatatac ggagttgaca ctagaatgct taccaaaatt ataagagaca aaggtactat   2520
gctgggaaaa attgagtttg aaggacagcc cgtggatttc gtagacccta ataagcagaa   2580
tcttatcgcc gaggtgagca caaaggacgt taaggtctac ggaaaaggaa atccaactaa   2640
ggtggtggct gttgattgtg gcattaagaa caacgtgatc agactgctgg tgaaacgcgg   2700
agctgaagtc catcttgtcc catggaatca tgattttacg aaaatggagt atgatggaat   2760
tctcatcgcc ggcggaccag ggaacccagc cttggctgaa ccccttatcc aaaacgttag   2820
aaaaatactc gaatctgata ggaaagagcc ccttttggt atatccaccg gaaacttgat    2880
tacaggcctt gctgcagggg ccaagacata taagatgagc atggcaaacc gcggacagaa   2940
tcagcccgta ctgaacatta ctaataagca ggcttttatc accgcacaga atcacggtta   3000
cgctctcgat aatacgctcc ctgccggctg gaagccgctc ttcgttaacg taaatgatca   3060
gacaaacgag ggaataatgc acgaatccaa acccttcttc gccgtccagt tccaccctga   3120
agtcactcca ggccctattg acacagaata tctctttgac tccttcttta gcctgataaa   3180
aaaggggaag gccaccacca taacgtccgt cctgcctaag ccagctctcg tggcatcaag   3240
agtagaggtc tccaaagtgc tcatacttgg tagcggggga ctgtcaatcg gccaagcagg   3300
cgagttcgat tactccggaa gccaagcagt taaggctatg aaagaagaga cgttaaaac   3360 tgtgctgatg aatccaaata tagcctccgt gcagaccaat gaggtgggtc tcaagcaagc   3420
agatactgtt tactttcttc caattacccc ccaattcgta accgaagtca ttaaggccga   3480
gcagcctgat ggattgatcc tgggtatggg cggacagact gcactgaatt gcggagtgga   3540
gttgttcaaa aggggtgtgt tgaaggaata tggagttaag gtactcggca cctccgttga   3600
gagcatcatg gcgaccgagg atagacagtt gttctctgat aaactgaacg agattaatga   3660
gaagatcgcc ccctcattcg ccgtggagtc tatcgaagat gcactgaaag ccgctgatac   3720
gattggctat cctgtaatga taagaagcgc ctacgccctg ggtggcctgg ggtctggcat   3780
ctgccctaac cgagagacgc tgatggacct ctccacaaaa gccttcgcca tgactaacca   3840
gattctggta gaaaaatccg tcaccggctg gaaggaaatt gaatacgaag tagtaagaga   3900
cgctgatgac aattgcgtca cagtctgcaa catggaaaac gtcgatgcga tgggcgtgca   3960
caccggagat tccgtcgttg tggcgccagc acaaacactc tccaatgctg agttccagat   4020
gctcagaaga acaagcatta acgttgtgcg acatcttggg atagttggcg aatgtaacat   4080
ccaatttgca ctgcacccaa ctagcatgga atactgcatt atcgaagtga atgcgcggct   4140
gagccgtcga ggacggggtg aactacgcct gaggatccga tcttttttccc tctgccaaaa   4200 attatgggga catcatgaag ccccttgagc atctgacttc tggctaataa aggaaattta   4260
ttttcattgc aatagtgtgt tggaattttt tgtgtctctc actcggaagc aattcgttga   4320
tctgaatttc gaccacccat aatacccatt accctggtag ataagtagca tggcgggtta   4380
atcattaact acaaggaacc cctagtgatg gagttggcca ctccctctct gcgcgctcgc   4440
tcgctcactg aggccgggcg accaaggtc gcccgacgcc cgggctttgc ccgggcggcc   4500
tcagtgagcg agcgagcgcg cagccttaat taacctaatt cactggccgt cgttttacaa   4560
cgtcgtgact gggaaaaccc tggcgttacc caacttaatc gccttgcagc acatccccct   4620
ttcgccagct ggcgtaatag cgaagaggcc cgcaccgatc gcccttccca acagttgcgc   4680
```

-continued

```
agcctgaatg gcgaatggga cgcgccctgt agcggcgcat taagcgcggc gggtgtggtg    4740
gttacgcgca gcgtgaccgc tacacttgcc agcgccctag cgcccgctcc tttcgctttc    4800
ttcccttcct ttctcgccac gttcgccggc tttccccgtc aagctctaaa tcggggggctc    4860 cctttagggt tccgatttag tgctttacgg cacctcgacc ccaaaaaact tgattagggt    4920
gatggttcac gtagtgggcc atcgccctga tagacggttt ttcgcccttt gacgttggag    4980
tccacgttct ttaatagtgg actcttgttc caaactggaa caacactcaa ccctatctcg    5040
gtctattctt ttgatttata agggattttg ccgatttcgg cctattggtt aaaaaatgag    5100
ctgatttaac aaaaatttaa cgcgaatttt aacaaaatat taacgcttac aatttaggtg    5160
gcacttttcg gggaaatgtg cgcggaaccc ctatttgttt attttttctaa atacattcaa    5220 atatgtatcc gctcatgaga caataaccct gataaatgct tcaataatat tgaaaaagga    5280
agagtatgag tattcaacat ttccgtgtcg cccttattcc cttttttgcg gcattttgcc    5340
ttcctgtttt tgctcaccca gaaacgctgg tgaaagtaaa agatgctgaa gatcagttgg    5400
gtgcacgagt gggttacatc gaactggatc tcaacagcgg taagatcctt gagagttttc    5460
gccccgaaga acgttttcca atgatgagca cttttaaagt tctgctatgt ggcgcggtat    5520
tatcccgtat tgacgccggg caagagcaac tcggtcgccg catacactat tctcagaatg    5580
acttggttga gtactcacca gtcacagaaa agcatcttac ggatggcatg acagtaagag    5640
aattatgcag tgctgccata accatgagtg ataacactgc ggccaactta cttctgacaa    5700
cgatcggagg accgaaggag ctaaccgctt ttttgcacaa catgggggat catgtaactc    5760
gccttgatcg ttgggaaccg gagctgaatg aagccatacc aaacgacgag cgtgacacca    5820
cgatgcctgt agcaatggca acaacgttgc gcaaactatt aactggcgaa ctacttactc    5880
tagcttcccg gcaacaatta atagactgga tggaggcgga taaagttgca ggaccacttc    5940
tgcgctcggc ccttccggct ggctggttta ttgctgataa atctggagcc ggtgagcgtg    6000
ggtctcgcgg tatcattgca gcactggggc cagatggtaa gccctcccgt atcgtagtta    6060
tctacacgac ggggagtcag gcaactatgg atgaacgaaa tagacagatc gctgagatag    6120
gtgcctcact gattaagcat tggtaactgt cagaccaagt ttactcatat atactttaga    6180
ttgatttaaa acttcatttt taatttaaaa ggatctaggt gaagatcctt tttgataatc    6240
tcatgaccaa aatcccttaa cgtgagtttt cgttccactg agcgtcagac cccgtagaaa    6300
agatcaaagg atcttcttga gatcctttt ttctgcgcgt aatctgctgc ttgcaaacaa    6360
aaaaaccacc gctaccagcg gtggtttgtt tgccggatca agagctacca actctttttc    6420
cgaaggtaac tggcttcagc agagcgcaga taccaaatac tgttcttcta gtgtagccgt    6480
agttaggcca ccacttcaag aactctgtag caccgcctac atacctcgct ctgctaatcc    6540
tgttaccagt ggctgctgcc agtggcgata agtcgtgtct taccgggttg gactcaagac    6600
gatagttacc ggataaggcg cagcggtcgg gctgaacggg gggttcgtgc acacagccca    6660
gcttggagcg aacgacctac accgaactga gatacctaca gcgtgagcta tgagaaagcg    6720
ccacgcttcc cgaagggaga aaggcggaca ggtatccggt aagcggcagg gtcggaacag    6780
gagagcgcac gagggagctt ccaggggg aa acgcctggta tctttatagt cctgtcgggt    6840
ttcgccacct ctgacttgag cgtcgatttt tgtgatgctc gtcagggggg cggagcctat    6900
ggaaaaacgc cagcaacgcg gcctttttac ggttcctggc cttttgctgg ccttttgctc    6960
acatgttctt tcctgcgtta tcccctgatt ctgtggataa ccgtattacc gcctttgagt    7020
gagctgatac cgctcgccgc agccgaacga ccgagcgcag cgagtcagtg agcgaggaag    7080
```

| | |
|---|---|
| cggaagagcg cccaatacgc aaaccgcctc tccccgcgcg ttggccgatt cattaatgca | 7140 |
| gctggcacga caggtttccc gactggaaag cgggcagtga gcgcaacgca attaatgtga | 7200 |
| gttagctcac tcattaggca ccccaggctt tacactttat gcttccggct cgtatgttgt | 7260 |
| gtggaattgt gagcggataa caatttcaca caggaaacag ctatgaccat gattacgcca | 7320 |
| gatttaatta aggccttaat tag | 7343 |

<210> SEQ ID NO 9
<211> LENGTH: 6216
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

| | |
|---|---|
| gctgcgcgct cgctcgctca ctgaggccgc ccgggcaaag cccgggcgtc gggcgacctt | 60 |
| tggtcgcccg gcctcagtga gcgagcgagc gcgcagagag ggagtggcca actccatcac | 120 |
| taggggttcc ttgtagttaa tgattaaccc gccatgctac ttatctacca gggtaatggg | 180 |
| gatctgccgt ggagtctatc gaagatgcac tgaaagccgc tgatacgatt ggctatcctg | 240 |
| taatgataag aagcgcctac gccctgggtg gcctggggtc tggcatctgc cctaaccgag | 300 |
| agacgctgat ggacctctcc acaaaagcct tcgccatgac taaccagatt ctggtagaaa | 360 |
| aatccgtcac cggctggaag gaaattgaat acgaagtagt aagagacgct gatgacaatt | 420 |
| gcgtcacagt ctgcaacatg gaaaacgtcg atgcgatggg cgtgcacacc ggagattccg | 480 |
| tcgttgtggc gccagcacaa acactctcca atgctgagtt ccagatgctc agaagaacaa | 540 |
| gcattaacgt tgtgcgacat cttgggatag ttggcgaatg taacatccaa tttgcactgc | 600 |
| acccaactag catggaatac tgcattatcg aagtgaatgc gcggctgagc cgaagcagcg | 660 |
| ctctcgccag caaagccaca ggctacccac ttgccttcat tgccgcaaag attgcactgg | 720 |
| gcattccact gcctgagatt aagaatgtcg taagcgggaa gacaagcgcc tgttttgaac | 780 |
| cttccctgga ctatatggtg actaagattc tccggtggga ccttgatagg ttccatggga | 840 |
| cctcatctag aataggatca tcaatgaagt ctgtgggtga agtgatggct atcgggcgga | 900 |
| ccttcgaaga gagttttcag aaagcacttc ggatgtgtca cccctcaatt gagggcttca | 960 |
| cccccggtt gccaatgaac aaggagtggc catcaaacct ggacctgaga aaagagctca | 1020 |
| gcgagcctag ctcaactaga atctacgcaa tcgccaaggc aatcgacgat aacatgtcat | 1080 |
| tggatgagat agagaagttg acatacatag acaaatggtt cctctacaaa atgcgagaca | 1140 |
| ttctgaatat ggagaaaaca ctgaagggac tgaattctga gagcatgacg gaggagacac | 1200 |
| ttaagagagc aaaagagatt gggttcagcg ataagcaaat ttcaaagtgc cttggactga | 1260 |
| ccgaagccca gacacgggag ctgagactga agaaaaatat acacccatgg gtgaagcaga | 1320 |
| tcgacacccct ggcggccgaa tatcccagcg ttactaatta cctgtatgtt acatataacg | 1380 |
| gccaagagca tgacgtaaat tttgacgatc atggaatgat ggttttggga tgcggtccct | 1440 |
| accacattgg ctcttcagtg gagtttgatt ggtgcgcagt gagctccatt cggaccctca | 1500 |
| gacagcttgg aaaaaaaaca gtggtggtaa attgtaaccc ggagactgtg tcaaccgact | 1560 |
| tcgacgaatg cgacaagttg tattttgagg aattgagtct tgaaaggatt cttgatatct | 1620 |
| accatcagga agcatgcgga ggctgtatta tctcagtggg cggcagata cccaacaacc | 1680 |
| ttgctgtacc tctctataaa aacggtgtaa agatcatggg cacctctccc ctccagattg | 1740 |

```
acagggccga ggaccgctca attttcagtg ctgtgctgga cgaactcaaa gtcgctcaag    1800
ctccttggaa agctgttaat actcttaacg aggccctcga gttcgccaag tctgtggatt    1860
acccatgtct tcttcggccc tcctacgtgc tgtcaggatc cgcaatgaac gtcgtgttca    1920
gcgaggatga aatgaagaaa tttctggagg aggctacacg ggtgagtcaa gagcatcctg    1980
tggttttgac taagttcgtt gagggcgccc gggaagtcga gatggatgca gtcggtaaag    2040
atggacgggt aattagccac gcaattagtg aacacgtgga agatgccggg gtccattctg    2100
gcgacgccac tctcatgctg ccaacacaga caattagtca gggtgctata gagaaagtga    2160
aagatgcgac taggaagatc gcaaaagcct tcgcaatatc tggcccattt aacgtgcagt    2220
ttctcgtgaa aggtaacgac gtcctggtga tcgagtgtaa tctccgagcg tcacgatcct    2280
tcccttttcgt aagcaagacc ctcggcgtag actttattga cgtggccacg aaagttatga    2340
ttggagagaa tgtagacgag aaacacctcc ccactcttga ccatccgatc atccccgcgg    2400
attatgttgc catcaaggcc caatgttctc ttggccgcg cctgcgagac gctgatccca    2460
tcttgcgctg tgaaatggca agcacaggcg aagtagcatg cttcggcgaa ggtattcata    2520
ccgcatttct gaaggccatg ctgagcaccg gcttcaagat cccccagaag ggtatcctca    2580
tcggcatcca gcagtctttc cgcccaagat tcctgggggt agcagaacaa cttcataacg    2640
aaggcttcaa gctgtttgca acagaagcaa cctctgattg gctgaacgct aataatgttc    2700
ctgcgactcc agtcgcctgg cccagccagg aaggacaaaa tcccagcctg tctagcatca    2760
gaaaactcat acgagatggc tctatcgacc ttgttatcaa cctgcctaat aacaacacca    2820
aatttgtcca cgacaactac gtcatcagaa gaactgccgt ggatagcggt atcccctgc     2880
tgaccaattt ccaggttacc aagctctttg cagaagctgt tcagaaatct cgcaaggtgg    2940
atagcaagtc actgtttcac tatcgacaat attcagcggg gaaggctgca taggcggccg    3000
caccggtaag cttggtacca ctagtcatat gttaattaag tcgacagatc cgatcttttt    3060
ccctctgcca aaaattatgg ggacatcatg aagcccttg agcatctgac ttctggctaa    3120
taaaggaaat ttattttcat tgcaatagtg tgttggaatt ttttgtgtct ctcactcgga    3180
agcaattcgt tgatctgaat ttcgaccacc cataataccc attccctgg tagataagta     3240
gcatggcggg ttaatcatta actacaagga acccctagtg atggagttgg ccactccctc    3300
tctgcgcgct cgctcgctca ctgaggccgg gcgaccaaag gtcgcccgac gcccgggctt    3360
tgcccgggcg gcctcagtga gcgagcgagc gcgcagcctt aattaaccta attcactggc    3420
cgtcgtttta caacgtcgtg actgggaaaa ccctggcgtt acccaactta atcgccttgc    3480
agcacatccc cctttcgcca gctggcgtaa tagcgaagag gcccgcaccg atcgcccttc    3540
ccaacagttg cgcagcctga atggcgaatg ggacgcgccc tgtagcggcg cattaagcgc    3600
ggcgggtgtg gtggttacgc gcagcgtgac cgctacactt gccagcgccc tagcgcccgc    3660
tcctttcgct ttcttccctt cctttctcgc cacgttcgcc ggctttcccc gtcaagctct    3720
aaatcggggg ctccctttag ggttccgatt tagtgcttta cggcacctcg accccaaaaa    3780
acttgattag ggtgatggtt cacgtagtgg gccatcgccc tgatagacgg ttttcgccc     3840
tttgacgttg gagtccacgt tctttaatag tggactcttg ttccaaactg gaacaacact    3900
caaccctatc tcggtctatt cttttgattt ataagggatt tgccgatttc ggcctattg     3960
gttaaaaaat gagctgattt aacaaaaatt taacgcgaat tttaacaaaa tattaacgct    4020
tacaatttag gtggcacttt tcggggaaat gtgcgcggaa cccctatttg tttatttttc    4080
```

```
taaatacatt caaatatgta tccgctcatg agacaataac cctgataaat gcttcaataa    4140
tattgaaaaa ggaagagtat gagtattcaa catttccgtg tcgcccttat tcccttttt     4200 gcggcatttt gccttcctgt ttttgctcac ccagaaacgc tggtgaaagt aaaagatgct    4260
gaagatcagt tgggtgcacg agtgggttac atcgaactgg atctcaacag cggtaagatc    4320
cttgagagtt ttcgccccga agaacgtttt ccaatgatga gcacttttaa agttctgcta    4380
tgtggcgcgg tattatcccg tattgacgcc gggcaagagc aactcggtcg ccgcatacac    4440
tattctcaga atgacttggt tgagtactca ccagtcacag aaaagcatct tacggatggc    4500
atgacagtaa gagaattatg cagtgctgcc ataaccatga gtgataacac tgcggccaac    4560
ttacttctga caacgatcgg aggaccgaag gagctaaccg cttttttgca acatgggg     4620 gatcatgtaa ctcgccttga tcgttgggaa ccggagctga atgaagccat accaaacgac    4680
gagcgtgaca ccacgatgcc tgtagcaatg gcaacaacgt tgcgcaaact attaactggc    4740
gaactactta ctctagcttc ccggcaacaa ttaatagact ggatggaggc ggataaagtt    4800
gcaggaccac ttctgcgctc ggcccttccg gctggctggt ttattgctga taaatctgga    4860
gccggtgagc gtgggtctcg cggtatcatt gcagcactgg ggccagatgg taagccctcc    4920
cgtatcgtag ttatctacac gacggggagt caggcaacta tggatgaacg aaatagacag    4980
atcgctgaga taggtgcctc actgattaag cattggtaac tgtcagacca agtttactca    5040
tatatacttt agattgattt aaaacttcat ttttaattta aaaggatcta ggtgaagatc    5100
ctttttgata atctcatgac caaaatccct taacgtgagt tttcgttcca ctgagcgtca    5160
gaccccgtag aaaagatcaa aggatcttct tgagatcctt ttttctgcg cgtaatctgc     5220 tgcttgcaaa caaaaaaacc accgctacca gcggtggttt gtttgccgga tcaagagcta    5280
ccaactcttt ttccgaaggt aactggcttc agcagagcgc agataccaaa tactgttctt    5340
ctagtgtagc cgtagttagg ccaccacttc aagaactctg tagcaccgcc tacatacctc    5400
gctctgctaa tcctgttacc agtggctgct gccagtggcg ataagtcgtg tcttaccggg    5460
ttggactcaa gacgatagtt accggataag gcgcagcggt cgggctgaac ggggggttcg    5520
tgcacacagc ccagcttgga gcgaacgacc tacaccgaac tgagatacct acagcgtgag    5580
ctatgagaaa gcgccacgct tcccgaaggg agaaaggcgg acaggtatcc ggtaagcggc    5640
agggtcggaa caggagagcg cacgagggag cttccagggg gaaacgcctg gtatctttat    5700
agtcctgtcg ggtttcgcca cctctgactt gagcgtcgat ttttgtgatg ctcgtcaggg    5760
gggcggagcc tatggaaaaa cgccagcaac gcggcctttt tacggttcct ggccttttgc    5820
tggccttttg ctcacatgtt ctttcctgcg ttatcccctg attctgtgga taaccgtatt    5880
accgcctttg agtgagctga taccgctcgc cgcagccgaa cgaccgagcg cagcgagtca    5940
gtgagcgagg aagcggaaga gcgcccaata cgcaaaccgc ctctccccgc gcgttggccg    6000
attcattaat gcagctggca cgacaggttt cccgactgga aagcgggcag tgagcgcaac    6060
gcaattaatg tgagttagct cactcattag gcaccccagg ctttacactt tatgcttccg    6120
gctcgtatgt tgtgtggaat tgtgagcgga taacaatttc acacaggaaa cagctatgac    6180
catgattacg ccagatttaa ttaaggcctt aattag                              6216
```

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic

```
        oligonucleotide

<400> SEQUENCE: 10
atgcctcaga                                                              10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 11
tgccgtggag                                                              10
```

TREATMENT FOR RESTORING UREAGENESIS IN CARBAMOYL PHOSPHATE SYNTHETASE 1 DEFICIENCY

CROSS REFERENCE TO RELATED APPLICATIONS

This application claims the benefit under 35 U.S.C. Section 119(e) of co-pending and commonly-assigned U.S. Provisional Patent Application Ser. No. 62/833,853, filed on Apr. 15, 2019 and entitled "TREATMENT FOR RESTORING UREAGENESIS IN CARBAMOYL PHOSPHATE SYNTHETASE 1 DEFICIENCY" which application is incorporated by reference herein.

STATEMENT REGARDING FEDERALLY SPONSORED RESEARCH AND DEVELOPMENT

This invention was made with government support under Grant Number NS091654, awarded by the National Institutes of Health. The government has certain rights in the invention.

TECHNICAL FIELD

The invention relates to methods and materials useful in treating Carbamoyl phosphate synthetase 1 (CPS1) deficiency.

BACKGROUND OF THE INVENTION

Carbamoyl phosphate synthetase 1 (CPS1) deficiency is a metabolic disorder of the liver that results in abnormal nitrogen metabolism and causes ammonia to accumulate in the blood (hyperammonemia). Ammonia, which is formed when proteins are broken down in the body, is toxic if the levels become too high. The brain is especially sensitive to the effects of excess ammonia. In the first few days of life, infants with carbamoyl phosphate synthetase I deficiency typically exhibit the effects of hyperammonemia, which may include poorly regulated breathing rate or body temperature, unusual body movements, seizures, or coma. Affected individuals who survive the newborn period may experience recurrence of these symptoms if diet is not carefully managed or if they experience infections or other stressors. They may also have delayed development and intellectual disability. In some people with carbamoyl phosphate synthetase I deficiency, signs and symptoms may be less severe and appear later in life.

In vivo, CPS1 catalyzes the first committed, rate-limiting step of the urea cycle by condensing ammonia and bicarbonate into carbamoyl phosphate. Loss or dysfunction of CPS1 activity results in elevated plasma ammonia, aberrant serum amino acid levels, cerebral edema, ataxia, and death if untreated. Current treatment for CPS1 deficiency consists primarily of dietary protein restriction, which is only marginally effective and leaves patients vulnerable to recurrent hyperammonemia and progressive, irreversible neurological decline.

There is an unmet need for patients affected with neonatal and late onset CPS1 deficiency. The neonatal form, which is quite severe, may be the most challenging urea cycle disorder to treat. Gene addition of CPS1 is an attractive alternative strategy for treating CPS1 deficiency but presents unique challenges. In view of this, there is a need for new methods and materials useful to address CPS1 deficiency.

SUMMARY OF THE INVENTION

Adeno-associated virus (AAV) is a small virus that infects humans which is useful as a vector to deliver genes to treat human genetic disorders. The carbamoyl phosphate synthetase 1 cDNA is 4500 bp which, when combined with other cis regulatory elements, exceeds the classical AAV genome capacity. Larger capacity lentiviruses and adenoviruses may accommodate CPS1, but issues remain with such vectors including unwanted genomic integration and immunogenicity. As discussed below, to overcome these limitations, split AAVs (sAAVs) that divide the CPS1 cDNA payload into two smaller overlapping CPS1 polynucleotide segments were designed, developed and tested. In embodiments of this invention, separate portions/segments of CPS1 were packaged into viruses individually and allowed to concatemerize in in vivo homologous recombination to reconstitute the transgenic payload and express the CPS1 protein following viral co-transduction of the same hepatocyte.

To illustrate the ability of sAAVs to treat CPS1 deficiency, sAAVs encoding human codon optimized CPS1 (hcoCPS1) driven by the constitutive CAG promoter were generated and tested in a conditional CPS1 knock out mouse model (see, e.g. Khoja et al., Molecular Genetics and Metabolism. 2018 Aug. 1; 124(4):243-253). When administered to mice having knocked out endogenous CPS1 expression, mice from this model demonstrate control of plasma ammonia following the administration of sAAVs comprising CPS1 polynucleotide sequences (which leads to the expression of the CPS1 protein in these mice). While all control mice perish, the mice treated with sAAVs comprising CPS1 polynucleotide sequences of the invention in this model live and have normal behavior. Currently, there is no effective therapy for human patients with CPS1 disorders. Our data from this gene therapy model in mice having knocked out endogenous CPS1 expression provides evidence that this treatment can address this unmet need for these patients.

The invention disclosed herein has a number of embodiments. For example, embodiments of the invention include methods of making pharmaceutical compositions useful in gene therapy. Such methods typically comprise comprising combining together in a formulation at least one adeno-associated viral vector comprising at least a portion of a codon optimized carbamoyl phosphate synthetase 1 polynucleotide sequence (SEQ ID NO: 2); and a pharmaceutical excipient selected from the group consisting of a preservative, a tonicity adjusting agent, a detergent, a viscosity adjusting agent, a sugar or a pH adjusting agent. Typically in these methods, the components of the pharmaceutical composition are selected so that when the adeno-associated viral vector(s) in the composition infect a human liver cell, carbamoyl phosphate synthetase 1 protein (SEQ ID NO: 1) is expressed. Typically, the adeno-associated viral vector(s) also comprise additional polynucleotide sequences selected to facilitate the expression of the CPS1 protein in a target cell population such as one or more polynucleotide sequences comprising a terminal repeat, a promoter (e.g. a tissue specific promoter), an enhancer, a chimeric intron; a polynucleotide sequence comprising a polyA signal and the like.

In some embodiments of the invention, the method of making pharmaceutical compositions useful in gene therapy combines two adeno-associated viral vectors in the pharmaceutical composition, a first adeno-associated viral vector comprising a first segment of a codon optimized carbamoyl phosphate synthetase 1 polynucleotide (SEQ ID NO: 2); and a second adeno-associated viral vector comprising a second segment of a codon optimized carbamoyl phosphate synthetase 1 polynucleotide (SEQ ID NO: 2). In such embodiments, the first adeno-associated viral vector comprising the first segment of a codon optimized carbamoyl phosphate synthetase 1 polynucleotide and the second adeno-associated viral vector comprising the second segment of a codon optimized carbamoyl phosphate synthetase 1 polynucleotide are selected so that the first and second segments of the carbamoyl phosphate synthetase 1 polynucleotides overlap such that, following first and second adeno-associated viral vector infection of the human liver cell, the carbamoyl phosphate synthetase 1 polynucleotides concatemerize via homologous recombination so as to reconstitute a carbamoyl phosphate synthetase 1 gene that expresses the carbamoyl phosphate synthetase 1 protein (SEQ ID NO: 1) in the liver cell.

Other embodiments of the invention include pharmaceutical compositions comprising a at least one adeno-associated viral vector comprising a polynucleotide sequence comprising a codon optimized polynucleotide sequence comprising at least a segment of a codon optimized gene encoding a carbamoyl phosphate synthetase 1 protein (SEQ ID NO: 1) in combination with a pharmaceutical excipient selected from the group consisting of a preservative, a tonicity adjusting agent, a detergent, a viscosity adjusting agent, a sugar or a pH adjusting agent. Typically, the adeno-associated viral vector(s) also comprise a terminal repeat, a polynucleotide sequence comprising a promoter, polynucleotide sequence comprising an enhancer, a polynucleotide sequence comprising a chimeric intron, and/or a polynucleotide sequence comprising a polyA signal. In certain embodiments of the invention, the composition comprises an adeno-associated viral vector comprising all of a codon optimized carbamoyl phosphate synthetase 1 polynucleotide sequence (SEQ ID NO: 2) which, when transduced into a human liver cell expresses the carbamoyl phosphate synthetase 1 protein (SEQ ID NO: 1). Typically however, the pharmaceutical compositions of the invention comprise a first and a second adeno-associated viral vector, both comprising codon optimized polynucleotide sequences of SEQ ID NO: 2 encoding a segment of the carbamoyl phosphate synthetase 1 protein (SEQ ID NO: 1). In such compositions, the first and second segments of the phosphate synthetase 1 polynucleotides in the different adeno-associated viral vectors are selected to overlap so that, following the first and second adeno-associated viral vector infection of a human liver cell, the carbamoyl phosphate synthetase 1 polynucleotides in the two vectors concatemerize via homologous recombination so as to reconstitute an operable carbamoyl phosphate synthetase 1 gene that expresses the carbamoyl phosphate synthetase 1 protein (SEQ ID NO: 1) in the liver cell. Optionally in such embodiments, the first segment of the carbamoyl phosphate synthetase 1 polynucleotide and the second segment of the carbamoyl phosphate synthetase 1 polynucleotide comprise at least 500 overlapping nucleotides of the carbamoyl phosphate synthetase 1 gene (SEQ ID NO: 2). Typically, at least one adeno-associated viral vector also comprises one or more additional polynucleotide sequences selected to facilitate the expression of the CPS1 protein in a target cell population such as one or more polynucleotide sequences comprising a terminal repeat, a promoter (e.g. a tissue specific promoter), an enhancer, a chimeric intron; a polynucleotide sequence comprising a polyA signal and the like.

Related embodiments of the invention include using the compositions disclosed herein in gene therapy methods to treat carbamoyl phosphate synthetase 1 (CPS1) deficiency. Such methods include, for example methods of delivering codon optimized carbamoyl phosphate synthetase 1 polynucleotides of SEQ ID NO: 2 into human cells comprising contacting a composition disclosed herein with human cells so that adeno-associated vector(s) infect the cells, thereby delivering the polynucleotides into the cells. In certain embodiments of the invention, the cells are in vivo liver cells, for example in vivo liver cells present in a mammal diagnosed with a carbamoyl phosphate synthetase I deficiency. Related embodiments of the invention include methods of treating a subject diagnosed with a carbamoyl phosphate synthetase 1 deficiency, comprising selecting a subject with a carbamoyl phosphate synthetase 1 deficiency and administering to the subject a therapeutically effective amount of a pharmaceutical composition disclosed herein. In some embodiments, the AAV (e.g. a sAAV) is administered intravenously.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIGS. 2A and 2B show graphs of data showing that CPS1 deficient mice (see, e.g. Khoja et al., Molecular Genetics and Metabolism. 2018 Aug. 1; 124(4):243-253) treated with split AAV-CPS1 vector constructs survive with treatment with Carglumic acid. Carglumic acid, marketed under the trade name Carbaglu, is used for the treatment of hyperammonaemia in patients with N-acetylglutamate synthase deficiency (see, e.g. Caldovic et al., (2004), J Pediatr. 145 (4): 552-4 and Elpeleg et al., (2002) Ann Neurol. 52 (6): 845-9). FIG. 2A shows the mean weight of mice treated with embodiments of the invention while FIG. 2B shows the survival of mice treated with embodiments of the invention.

DETAILED DESCRIPTION OF THE INVENTION

Figure 1:
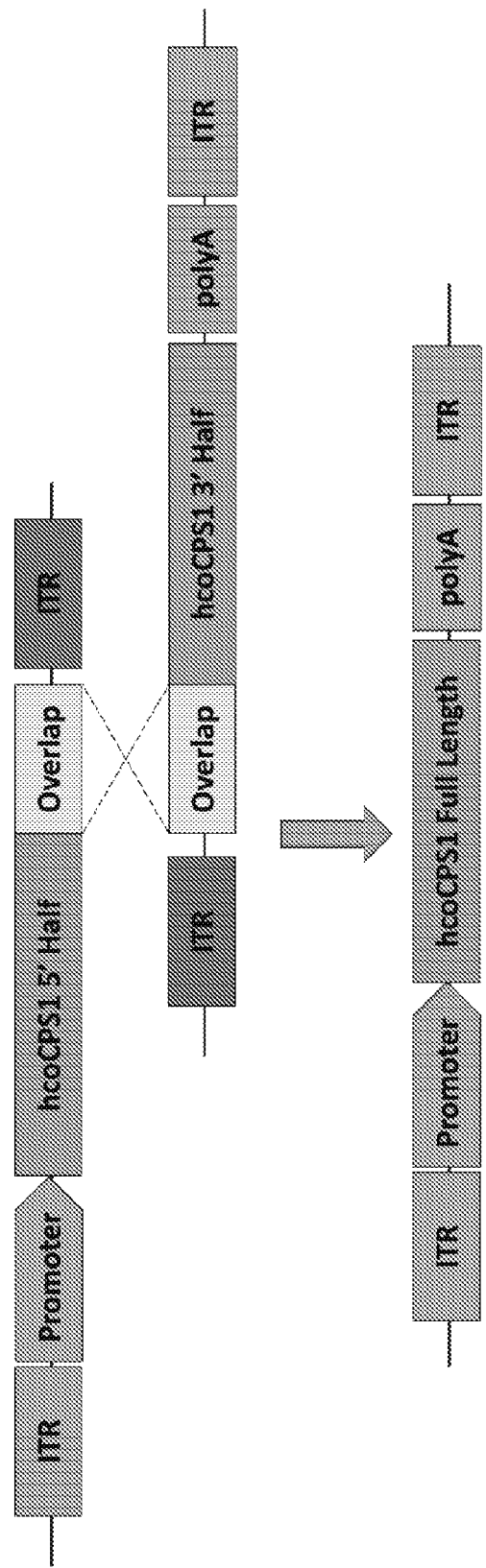
FIG. 1 shows a cartoon schematic showing an illustrative split AAV-CPS1 vector constructs and concatemerization in vivo via homologous recombination (i.e. to reconstitute the transgenic payload after co-transduction of a hepatocyte).
Figure 3A:
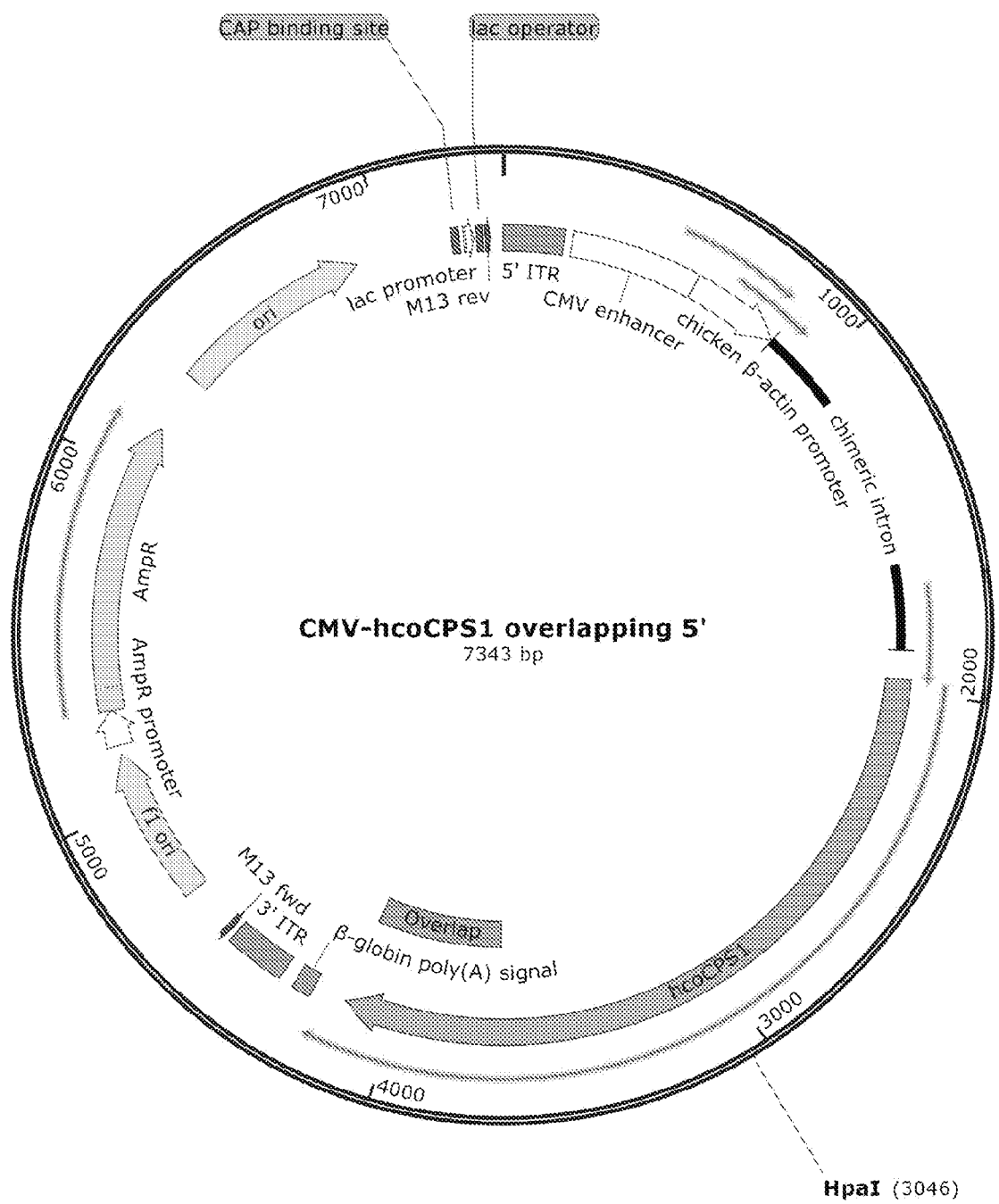
FIGS. 3A and 3B show cartoon schematics of illustrative working embodiments of a first adeno-associated viral vector comprising a first segment of a codon optimized carbamoyl phosphate synthetase 1 polynucleotide (FIG. 3A, SEQ ID NO: 8) and a second adeno-associated viral vector comprising a second segment of a codon optimized carbamoyl phosphate synthetase 1 polynucleotide (FIG. 3B, SEQ ID NO: 9).
Figure 3B:
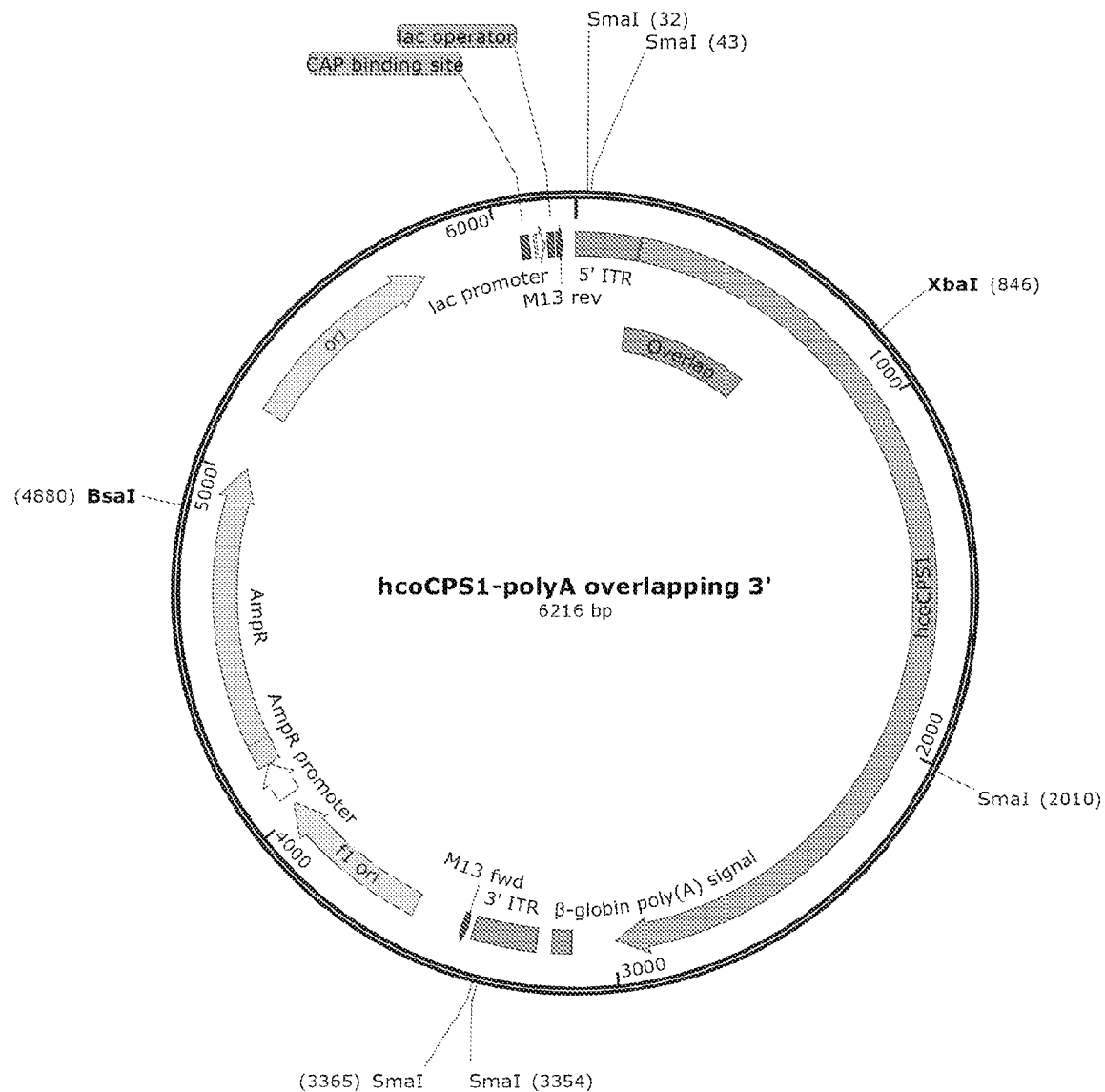

In the description of embodiments, reference may be made to the accompanying figures which form a part hereof, and in which is shown by way of illustration a specific embodiment in which the invention may be practiced. It is to be understood that other embodiments may be utilized, and structural changes may be made without departing from the scope of the present invention. Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

All publications mentioned herein are incorporated herein by reference to disclose and describe aspects, methods and/or materials in connection with the cited publications (e.g. U.S. Patent Application Publication Numbers 20060115869, 20080176259, 20090311719, 20100183704, 20180163229 and 20190017069, and Diez-Fernandez C et al. Expert Opin Ther Targets, 2017 April; 21(4):391-399, doi: 10.1080/14728222.2017.1294685, Zhang G et al. J Clin Lab Anal. 2018 February; 32(2), doi: 10.1002/jcla.22241, Choi R et al. Ann Lab Med. 2017 January; 37(1):58-62, doi: 10.3343/alm.2017.37.1.58, Naso et al., BioDrugs (2017) 31:317-334, and Srinivasan et al., J Inherit Metab Dis. 2019 Mar. 6, doi: 10.1002/jimd.12067).

Throughout development and adulthood, the liver carries out a broad range of essential metabolic processes, including protein catabolism. Protein breakdown generates ammonia as a byproduct, which is detoxified primarily by the urea cycle. Carbamoyl phosphate synthetase 1 protein catalyzes the first committed, rate-limiting step of the urea cycle by condensing ammonia and bicarbonate into carbamoyl phosphate. Loss or dysfunction of CPS1 activity results in elevated plasma ammonia, aberrant serum amino acid levels, cerebral edema, and death if untreated. Current treatment for CPS1 deficiency consists primarily of dietary protein restriction, which is only marginally effective and leaves patients vulnerable to recurrent hyperammonemia and progressive, irreversible neurological decline. Liver transplantation is the only curative option but is limited by organ availability and the need for immune suppression. Gene addition of CPS1 is therefore an attractive alternative strategy for treating CPS1 deficiency but also presents unique challenges. CPS1 cDNA is 4.5 kb which, when combined with other cis regulatory elements, exceeds the classical AAV genome capacity. Larger capacity lentiviruses and adenoviruses may accommodate CPS1, but issues remain with non AAV vectors such as unwanted genomic integration and immunogenicity.

To overcome the limitations of classical AAV genome capacity, split AAVs (sAAVs) that divide the payload into two overlapping portions were developed (i.e. two AAV vectors that that contain portions of the same CPS1 polynucleotide sequence). The separate portions are packaged into viruses individually and concatemerize via homologous recombination to reconstitute the transgenic payload and express the CPS1 protein in cells after the co-transduction of cells (see the illustration of this in FIG. 1). To determine the ability of sAAVs to treat CPS1 deficiency, sAAVs encoding human codon optimized CPS1 (hcoCPS1) driven by the constitutive CAG promoter were then generated. These sAAVs are shown to successfully concatemerize and express hcoCPS1 mRNA and protein in cells transduced with these vectors.

The invention disclosed herein has a number of embodiments. Embodiments of the invention include methods of making pharmaceutical compositions useful in gene therapy. Such methods typically comprise comprising disposing in an aqueous formulation at least one adeno-associated viral vector comprising at least a portion/segment (e.g. a plurality of at least 100, 500 or 1000 contiguous nucleic acids), and optionally a complete codon optimized carbamoyl phosphate synthetase 1 ("CPS 1") polynucleotide sequence (SEQ ID NO: 2) that encodes the carbamoyl phosphate synthetase 1 protein (SEQ ID NO: 1). These compositions typically further include a pharmaceutical excipient selected from the group consisting of a preservative, a tonicity adjusting agent, a detergent, a viscosity adjusting agent, a sugar or a pH adjusting agent. Typically in these methods, the components of the pharmaceutical composition are selected so that when the adeno-associated viral vector(s) in the composition infect a human liver cell, a carbamoyl phosphate synthetase 1 protein (SEQ ID NO: 1) is expressed. Typically, the at least one adeno-associated viral vector(s) also comprise additional polynucleotide sequences selected to facilitate the expression of the CPS1 protein in a target cell population such as one or more polynucleotide sequences comprising a terminal repeat, a promoter (e.g. a tissue specific promoter), an enhancer, a chimeric intron; a polynucleotide sequence comprising a polyA signal and the like.

In some embodiments of the invention, the method of making pharmaceutical compositions useful in gene therapy combines two adeno-associated viral vectors in the pharmaceutical composition, a first adeno-associated viral vector comprising a first segment of a codon optimized carbamoyl phosphate synthetase 1 polynucleotide (SEQ ID NO: 2); and a second adeno-associated viral vector comprising a second segment of a codon optimized carbamoyl phosphate synthetase 1 polynucleotide (SEQ ID NO: 2). In such embodiments, the first adeno-associated viral vector comprising the first segment of a codon optimized carbamoyl phosphate synthetase 1 polynucleotide and the second adeno-associated viral vector comprising the second segment of a codon optimized carbamoyl phosphate synthetase 1 polynucleotide are selected so that the first and second segments of the carbamoyl phosphate synthetase 1 polynucleotides overlap such that, following first and second adeno-associated viral vector infection of the human liver cell, the carbamoyl phosphate synthetase 1 polynucleotides concatemerize via homologous recombination so as to reconstitute a carbamoyl phosphate synthetase 1 gene that expresses the carbamoyl phosphate synthetase 1 protein (SEQ ID NO: 1) in the liver cell.

Other embodiments of the invention include pharmaceutical compositions comprising a at least one adeno-associated viral vector comprising at least a segment of a codon optimized carbamoyl phosphate synthetase 1 polynucleotide sequence (SEQ ID NO: 2) that encodes at least a segment of a carbamoyl phosphate synthetase 1 protein (SEQ ID NO: 1) in combination with a pharmaceutical excipient selected from the group consisting of a preservative, a tonicity adjusting agent, a detergent, a viscosity adjusting agent, a sugar or a pH adjusting agent. Typically, the kit includes at least two AAVs, each comprising some or all of the CPS1 gene, and at least one adeno-associated viral vector(s) also comprises a terminal repeat, a polynucleotide sequence comprising a promoter, polynucleotide sequence comprising an enhancer, a polynucleotide sequence comprising a chimeric intron; and/or a polynucleotide sequence comprising a polyA signal.

In some embodiments of the invention, the composition comprises an adeno-associated viral vector comprising all of the carbamoyl phosphate synthetase 1 polynucleotide sequence which, when transduced into a human liver cell expresses the carbamoyl phosphate synthetase 1 protein (SEQ ID NO: 1). Typically however, the pharmaceutical compositions of the invention comprise a first and a second adeno-associated viral vector, both comprising polynucleotide sequences encoding one or more segments of the carbamoyl phosphate synthetase 1 protein (SEQ ID NO: 1). In such compositions, first and second segments of the phosphate synthetase 1 polynucleotides in the different adeno-associated viral vectors are selected to overlap so that, following the first and second adeno-associated viral vector infection of a human liver cell, the carbamoyl phosphate synthetase 1 polynucleotides in the two vectors concatemerize via homologous recombination so as to reconstitute an operable carbamoyl phosphate synthetase 1 gene that expresses a functional carbamoyl phosphate synthetase 1 protein (SEQ ID NO: 1) in the liver cell. Optionally in such embodiments, the first segment of the carbamoyl phosphate synthetase 1 polynucleotide and the second segment of the carbamoyl phosphate synthetase 1 polynucleotide comprise at least 100 overlapping nucleotides of the codon optimized carbamoyl phosphate synthetase 1 gene (SEQ ID NO: 2). Typically, at least one of the adeno-associated viral vector(s) also comprises one or more additional polynucleotide sequences selected to facilitate the expression of the CPS1 protein in a target cell population such as one or more polynucleotide sequences comprising a terminal repeat, a promoter (e.g. a tissue specific promoter), an enhancer, a chimeric intron; a polynucleotide sequence comprising a polyA signal and the like.

Embodiments of the invention further include systems and kits comprising compositions of the invention. In some embodiments, the system comprises a composition that includes an adeno-associated viral vector comprising all of the carbamoyl phosphate synthetase 1 polynucleotide sequence which, when transduced into a human liver cell expresses the carbamoyl phosphate synthetase 1 protein (SEQ ID NO: 1). In some embodiments, a pharmaceutical composition of the system or kit comprises a combination of a first and a second adeno-associated viral vector, both comprising polynucleotide sequences encoding one or more segments of the carbamoyl phosphate synthetase 1 protein (SEQ ID NO: 1). In other embodiments, a first pharmaceutical composition comprises a first adeno-associated viral vector and a second pharmaceutical composition comprises a second adeno-associated viral vector, each individual vector comprising polynucleotide sequences encoding one or more segments of the carbamoyl phosphate synthetase 1 protein (SEQ ID NO: 1). In such compositions, first and second segments of the phosphate synthetase 1 polynucleotides in the different adeno-associated viral vectors are selected to overlap so that, following the first and second adeno-associated viral vector infection of a human liver cell, the carbamoyl phosphate synthetase 1 polynucleotides in the two vectors concatemerize via homologous recombination so as to reconstitute an operable carbamoyl phosphate synthetase 1 gene that expresses a functional carbamoyl phosphate synthetase 1 protein (SEQ ID NO: 1) in the liver cell.

Other embodiments of the invention include using the compositions disclosed herein in gene therapy methods to treat carbamoyl phosphate synthetase 1 (CPS1) deficiency. Such methods include, for example methods of delivering carbamoyl phosphate synthetase 1 polynucleotides into human cells comprising contacting a composition disclosed herein (e.g. a composition comprising a first adeno-associated viral vector in combination with a second adeno-associated viral vector having overlapping regions of the CPS1 gene) with human cells so that adeno-associated vector(s) infect the cells, thereby delivering the polynucleotides into the cells. In certain embodiments of the invention, the cells are in vivo liver cells, for example in vivo liver cells present in a mammal diagnosed with a carbamoyl phosphate synthetase I deficiency. Related embodiments of the invention include methods of treating a subject diagnosed with a carbamoyl phosphate synthetase 1 deficiency, comprising selecting a subject with a carbamoyl phosphate synthetase 1 deficiency and administering to the subject a therapeutically effective amount of a pharmaceutical composition disclosed herein. In some embodiments, the AAV (e.g. a sAAV) is administered intravenously.

Figure 4:
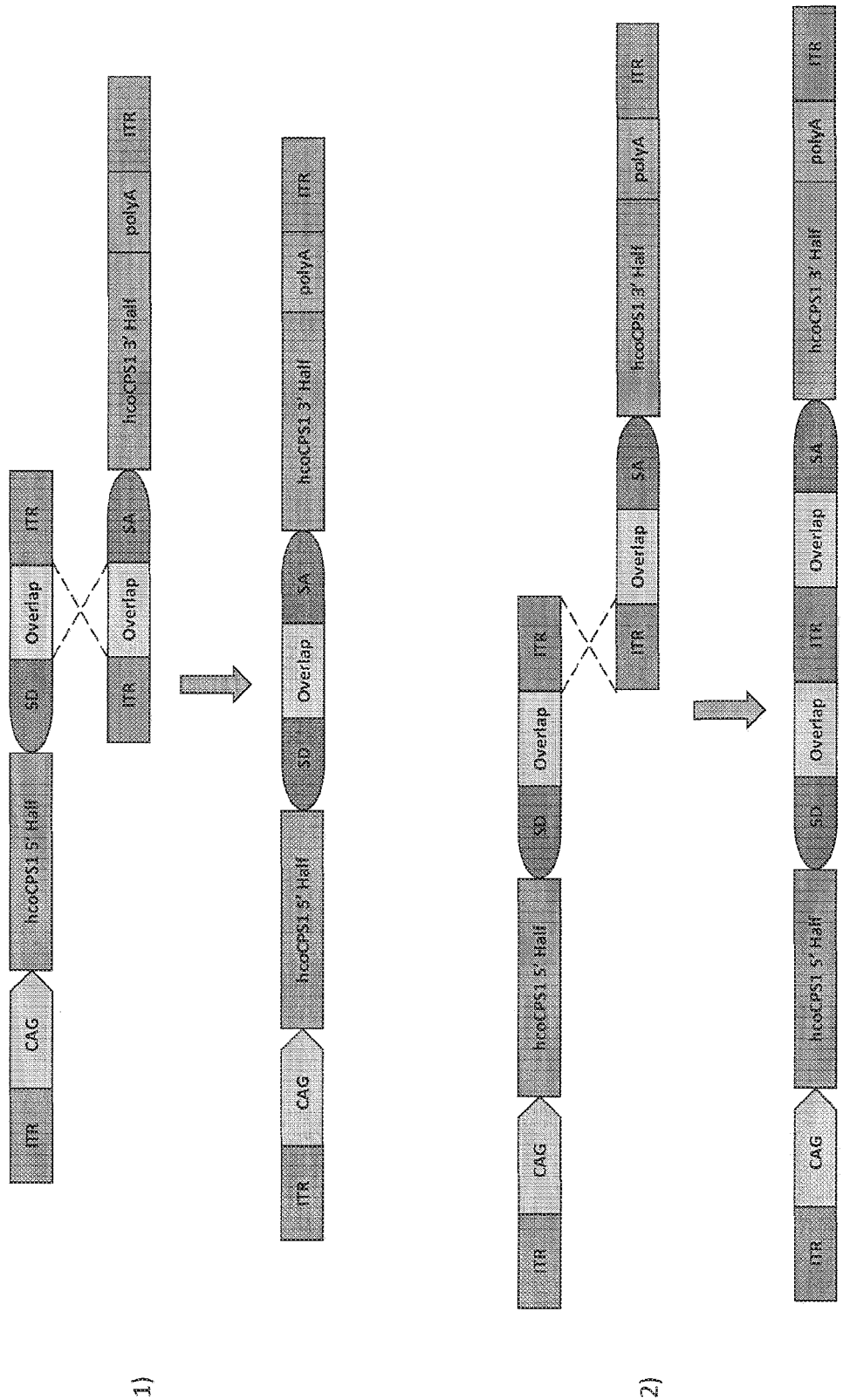
FIG. 4 shows a cartoon schematic showing illustrative a hybrid AAV-CPS1 vector construct where a human codon-optimized CPS1 transgene is split in half with no overlapping CPS1 sequences in the open reading frame and inserted into hybrid AAVs. In typical embodiments, a short, highly recombinogenic region from the alkaline phosphatase (AP) gene (or the like) with a splice donor (SD) site is added to the 3' end of the left half of the transgene; and the same AP fragment with a splice acceptor (SA) site is added to the 5' end of the right half of the transgene. Upon co-transduction of the hybrid sAAVs into mammalian cells, the hybrid sAAVs concatemerize in two orientations to reconstitute CPS1 transgene protein expression in a construct where: 1) AP-mediated recombination removes the intervening viral ITR and the full-length transgene is expressed with the AP fragment removed via splicing; 2) ITR-mediated recombination retains the intervening ITR, and the entire region encompassed by the splice sites (AP-ITR-AP) is removed during splicing.

While split AAVs having overlapping CPS1 polynucleotide segments for homologous recombination are one embodiment of the invention, other related embodiments are encompassed by the disclosure provided herein. For example, as an alternative to the split AAVs having an overlapping CPS1 segment for homologous recombination, a hybrid split AAV approach has been developed that builds upon other conventional technologies (e.g. Ghosh et al., A Hybrid Vector System Expands Adeno-associated Viral Vector Packaging Capacity in a Transgene-independent Manner. Molecular Therapy 16, 124-130 (2008)). In this alternative approach, an embodiment of which is shown in FIG. 4, a human codon-optimized CPS1 transgene is split in half with no overlapping CPS1 sequences in the open reading frame and inserted into hybrid AAVs. In such embodiments, a short, highly recombinogenic region from the alkaline phosphatase (AP) gene with a splice donor (SD) site is added to the 3' end of the left half of the transgene; and the same AP fragment with a splice acceptor (SA) site is added to the 5' end of the right half of the transgene. Upon co-transduction of the hybrid sAAVs into mammalian cells, the hybrid sAAVs concatemerize in two orientations to reconstitute CPS1 transgene protein expression in a construct where: 1) AP-mediated recombination removes the intervening viral ITR and the full-length transgene is expressed with the AP fragment removed via splicing; 2) ITR-mediated recombination retains the intervening ITR, and the entire region encompassed by the splice sites (AP-ITR-AP) is removed during splicing.

In illustrative embodiments of the invention, to test sAAV efficacy in vivo, a conditional CPS1 knock out mouse model was used. These mice contain biallelic floxed Cps1 which is removed by treatment with an AAV expressing Cre recombinase (AAV-Cre). Dose escalation studies with embodiments of the invention showed that the minimum dose of sAAVs necessary to modestly extend lifespan in Cre-treated mice is $3 \times 10^{14}$ gc/kg; therefore, a dose of $5 \times 10^{14}$ gc/kg was chosen to study long-term survival. Floxed CPS1 mice injected with AAV-Cre and sAAVs showed increased lifespan (>30 days; $p<0.01$) and reduced plasma ammonia compared to controls that received AAV-Cre alone, all perishing by day 22 (treated: 339.6 $\mu M \pm 94.5$; untreated: 1349.9 $\mu M \pm 379.6$ [mean±SD]; $p<0.01$). Over time we detected a slow decline in weight and rise in plasma ammonia, necessitating further intervention. Treatment with the small molecule n-carglumic acid, an analog of NAG, the allosteric activator of CPS1, further extended lifespan (all mice >120 days; $p<0.01$) and maintained near normal plasma ammonia (baseline: 138.87 $\mu M \pm 86.5$; post-treatment: 217.8 $\mu M \pm 69.9$; $p=0.15$). Immunohistochemical analysis demonstrated broad distribution of CPS1 throughout the liver parenchyma in sAAV-treated mice, while control mice showed only small loci of remaining expression inadequate to result in minimal necessary ureagenesis and survival. In conclusion, sAAV-mediated CPS1 expression extends lifespan, controls plasma ammonia, and maintains healthy weight and activity in a mouse model of this severe disorder of nitrogen metabolism.

As noted above, embodiments of the invention utilize adeno-associated virus (AAV). AAV is a non-enveloped virus that can be engineered to deliver DNA to target cells, which has attracted a significant amount of attention in the field, especially in clinical-stage experimental therapeutic strategies. The ability to generate recombinant AAV particles lacking any viral genes and containing DNA sequences of interest for various therapeutic applications has thus far proven to be one of the safest strategies for gene therapies. The review in Naso et al., BioDrugs (2017) 31:317-334 provides an overview of factors considered in the use of AAV as a vector for gene therapy. U.S. Patent Application Publication Numbers 20190017069 20180163227 20180104289 20170362670 20170348435 20170211095 20170304466 and 20170096682 disclose illustrative AAV methods and materials.

Compositions comprising AAV constructs (e.g. the sAAV constructs disclosed herein) of the invention can be formulated as pharmaceutical compositions in a variety of forms adapted to the chosen route of administration. The compounds of the invention are typically administered in combination with a pharmaceutically acceptable vehicle such as an inert diluent. For compositions suitable for administration to humans, the term "excipient" is meant to include, but is not limited to, those ingredients described in Remington: The Science and Practice of Pharmacy, Lippincott Williams & Wilkins, 21st ed. (2006) the contents of which are incorporated by reference herein.

The compounds may also be administered in a variety of ways, for example intravenously. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

Useful liquid carriers include water, alcohols or glycols or water/alcohol/glycol blends, in which the compounds can be dissolved or dispersed at effective levels, optionally with the aid of non-toxic surfactants. Adjuvants such as additional antimicrobial agents can be added to optimize the properties for a given use.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically using the disclosure presented herein, by conventional procedures known to those of skill in the art. See e.g., The Pharmacological Basis of Therapeutics, Goodman and Gilman, eds., Macmillan Publishing Co., New York, $13^{th}$ Edition. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

In certain embodiments of the invention, AAV constructs disclosed herein may be used for the preparation of a pharmaceutical composition for the treatment of disease. Such disease may comprise a disease treatable by gene therapy, including carbamoyl phosphate synthetase I deficiency. The term "pharmaceutical composition", as used herein, refers to a composition comprising a therapeutically effective amount of active agents of the present invention and at least one non-naturally occurring pharmaceutically acceptable excipient. Embodiments of the invention relate to pharmaceutical compositions comprising one or more AAV constructs disclosed herein in combination with a pharmaceutically acceptable excipient. In this context, embodiments of this invention include for example, a pharmaceutical composition comprising first adeno-associated viral vector combined with a second adeno-associated viral vector, each viral vector comprising a segment of a codon optimized carbamoyl phosphate synthetase 1 polynucleotide sequence of SEQ ID NO: 2, for use in the treatment of carbamoyl phosphate synthetase 1 deficiency disease, wherein the first and second segments of the carbamoyl phosphate synthetase 1 polynucleotides overlap such that, following first and second adeno-associated viral vector infection of a human liver cell, the carbamoyl phosphate synthetase 1 polynucleotides concatemerize via homologous recombination so as to reconstitute a carbamoyl phosphate synthetase 1 gene that expresses carbamoyl phosphate synthetase 1 protein of SEQ ID NO: 1 in the liver cell. Similar embodiments of the invention include two separate pharmaceutical compositions, one comprising the first adeno-associated viral vector and another one comprising the second adeno-associated viral vector (e.g. in pharmaceutical compositions that can be administered separately in methods of treating CPS1 deficiency). The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months.

The terms "pharmaceutically acceptable excipient", or "pharmaceutically acceptable carrier," "pharmaceutically acceptable diluent,", or "pharmaceutically acceptable vehicle," used interchangeably herein, refer to a non-toxic solid, semisolid or liquid filler, diluent, encapsulating material or formulation auxiliary of any conventional type. A pharmaceutically acceptable carrier is essentially non-toxic to recipients at the dosages and concentrations employed and is compatible with other ingredients of the formulation. Suitable carriers include, but are not limited to water, dextrose, glycerol, saline, ethanol, and combinations thereof. The carrier can contain additional agents such as wetting or emulsifying agents, pH buffering agents, or adjuvants which enhance the effectiveness of the formulation.

The person skilled in the art will appreciate that the nature of the excipient in the pharmaceutical composition of the invention will depend to a great extent on the administration route. In the case of the pharmaceutical compositions formulated for use in gene therapy regimens, a pharmaceutical composition according to the invention normally contains the pharmaceutical composition of the invention mixed with one or more pharmaceutically acceptable excipients. These excipients can be, for example, inert fillers or diluents, such as sucrose, sorbitol, sugar, mannitol, microcrystalline cellulose, starches, including potato starch, calcium carbonate, sodium chloride, lactose, calcium phosphate, calcium sulfate or sodium phosphate; crumbling agents and disintegrants, for example cellulose derivatives, including microcrystalline cellulose, starches, including potato starch, sodium croscarmellose, alginates or alginic acid and chitosans; binding agents, for example sucrose, glucose, sorbitol, acacia, alginic acid, sodium alginate, gelatin, starch, pregelatinized starch, microcrystalline cellulose, aluminum magnesium silicate, sodium carboxymethylcellulose, methylcellulose, hydroxypropyl methylcellulose, ethylcellulose, polyvinylpyrrolidone, polyvinyl acetate or polyethylene glycol, and chitosans; lubricating agents, including glidants and antiadhesive agents, for example magnesium stearate, zinc stearate, stearic acid, silicas, hydrogenated vegetable oils or talc.

The present invention further provides methods associated with gene therapy regimens such as methods of delivering a CPS1 nucleic acid to a cell. In such methods, the virus may be administered to the cell by standard viral transduction methods, as are known in the art. Preferably, the virus particles are added to the cells at the appropriate multiplicity of infection according to standard transduction methods appropriate for the particular target cells. Titers of virus to administer can vary, depending upon the target cell type and the particular virus vector, and may be determined by those of skill in the art without undue experimentation. Alternatively, administration of a AAV vector(s) of the present invention (e.g. the sAAV constructs disclosed herein) can be accomplished by any other means known in the art.

Recombinant AAV virus vectors are preferably administered to the cell in a biologically-effective amount. A "biologically-effective" amount of the virus vector is an amount that is sufficient to result in infection (or transduction) and expression of the heterologous nucleic acid sequence in the cell. If the virus is administered to a cell in vivo (e.g., the virus is administered to a subject as described below), a "biologically-effective" amount of the virus vector is an amount that is sufficient to result in transduction and expression of the heterologous nucleic acid sequence in a target cell. The cell to be administered the inventive virus vector may be of any type, including but not limited to hepatic cells.

A "therapeutically-effective" amount as used herein is an amount that is sufficient to alleviate (e.g., mitigate, decrease, reduce) at least one of the symptoms associated with a disease state (e.g. one caused by CPS1 deficiency). Alternatively stated, a "therapeutically-effective" amount is an amount that is sufficient to provide some improvement in the condition of the subject.

A further aspect of the invention is a method of treating subjects in vivo with the inventive viral constructs. Administration of the AAV constructs of the present invention to a human subject or an animal in need thereof can be by any means known in the art for administering virus vectors.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspensions in liquid prior to injection, or as emulsions. Alternatively, one may administer the virus in a local rather than systemic manner, for example in a depot or sustained-release formulation.

In particularly preformed embodiments of the invention, the nucleotide sequence(s) of interest is/are delivered to the liver of the subject. Administration to the liver may be achieved by any method known in art, including, but not limited to intravenous administration, intraportal administration, intrabilary administration, intra-arterial administration, and direct injection into the liver parenchyma. Typically for example, the liver cells are infected by sAAV vectors encoding segments of the CPS1 gene so that the CPS polynucleotides concatemerize via homologous recombination in the liver cells so as to reconstitute a carbamoyl phosphate synthetase 1 polynucleotide that expresses the carbamoyl phosphate synthetase 1 protein (SEQ ID NO: 1) in the liver cell cells. Optionally such methods are combined with another therapeutic modality, for example, the administration of Carglumic acid (Carbaglu).

The following disclosure provides illustrative amino acid and nucleic acid sequences of human carbamoyl phosphate synthetase 1 that can be used in embodiments of the invention as well as other elements/sequences that can be used in embodiments of the invention. Embodiments of the invention include, for example, adeno-associated viral vectors selected to have a number of elements that facilitate CPS1 expression in human cells (e.g. liver cells) such as terminal repeat sequences (e.g. ITRs), introns, promoters (e.g. a liver specific promoter), codon optimized CPS1 sequences, polyA signal sequences and the like. Such illustrative but nonlimiting sequences from the working embodiments of the invention disclosed herein are provided below.

SEQ ID NO: 1 below shows the Carbamoyl phosphate synthetase 1 Protein Sequence (*Homo sapiens*).

```
LOCUS       CAA75785                1500 aa
ACCESSION   CAA75785
ORGANISM    Homo sapiens
REFERENCE:  Finckh et al., "Prenatal diagnosis of
carbamoyl phosphate synthetase I deficiency by
identification of a missense mutation in CPS1"
Hum. Mutat. 12 (3), 206-211 (1998).
                                        (SEQ ID NO: 1)
MTRILTAFKVVRTLKTGFGFTNVTAHQKWKFSRPGIRLLSVKAQTAHIVL

EDGTKMKGYSFGHPSSYAGEVVFNTGLGGYPEAITDPAYKGQILTMANPI

IGNGGAPDTTALDELGLSKYLESNGIKVSGLLVLDYSKDYNHWLATKSLG

QWLQEEKVPAIYGVDTRMLTKIIRDKGTMLGKIEFEGQPVDFVDPNKQNL

IAEVSTKDVKVYGKGNPTKVVAVDCGIKNNVIRLLVKRGAEVHLVPWNHD

FTKMEYDGILIAGGPGNPALAEPLIQNVRKILESDRKEPLFGISTGNLIT

GLAAGAKTYKMSMANRGQNQPVLNITNKQAFITAQNHGYALDNTLPAGWK

PLFVNVNDQTNEGIMHESKPFFAVQFHPEVTPGPIDTEYLFDSFFSLIKK

GKATTITSVLPKPALVASRVEVSKVLILGSGGLSIGQAGEFDYSGSQAVK

AMKEENVKTVLMNPNIASVQTNEVGLKQADTVYFLPITPQFVTEVIKAEQ

PDGLILGMGGQTALNCGVELFKRGVLKEYGVKVLGTSVESIMATEDRQLF

SDKLNEINEKIAPSFAVESIEDALKAADTIGYPVMIRSAYALGGLGSGIC

PNRETLMDLSTKAFAMTNQILVEKSVTGWKEIEYEVVRDADDNCVTVCNM

ENVDAMGVHTGDSVVVAPAQTLSNAEFQMLRRTSINVVRHLGIVGECNIQ
```

-continued
```
FALHPTSMEYCIIEVNARLSRSSALASKATGYPLAFIAAKIALGIPLPEI

KNVVSGKTSACFEPSLDYMVTKIPRWDLDRFHGTSSRIGSSMKSVGEVMA

IGRTFEESFQKALRMCHPSIEGFTPRLPMNKEWPSNLDLRKELSEPSSTR

IYAIAKAIDDNMSLDEIEKLTYIDKWFLYKMRDILNMEKTLKGLNSESMT

EETLKRAKEIGFSDKQISKCLGLTEAQTRELRLKKNIHPWVKQIDTLAAE

YPSVTNYLYVTYNGQEHDVNFDDHGMMVLGCGPYHIGSSVEFDWCAVSSI

RTLRQLGKKTVVVNCNPETVSTDFDECDKLYFEELSLERILDIYHQEACG

GCIISVGGQIPNNLAVPLYKNGVKIMGTSPLQIDRAEDRSIFSAVLDELK

VAQAPWKAVNTLNEALEFAKSVDYPCLLRPSYVLSGSAMNVVFSEDEMKK

FLEEATRVSQEHPVVLTKFVEGAREVEMDAVGKDGRVISHAISEHVEDAG

VHSGDATLMLPTQTISQGAIEKVKDATRKIAKAFAISGPFNVQFLVKGND

VLVIECNLRASRSFPFVSKTLGVDFIDVATKVMIGENVDEKHLPTLDHPI

IPADYVAIKAPMFSWPRLRDADPILRCEMASTGEVACFGEGIHTAFLKAM

LSTGFKIPQKGILIGIQQSFRPRFLGVAEQLHNEGFKLFATEATSDWLNA

NNVPATPVAWPSQEGQNPSLSSIRKLIRDGSIDLVINLPNNNTKFVHDNY

VIRRTAVDSGIPLLTNFQVTKLFAEAVQKSRKVDSKSLFHYRQYSAGKAA
```

SEQ ID NO: 2 below shows Full-length codon optimized human Carbamoyl phosphate synthetase 1 polynucleotide sequence

```
                                        (SEQ ID NO: 2)
ATGCCTCAGATCATAAAGATGACCCGGATTCTTACCGCATTCAAGGTTGTAAGGACCCT

TAAAACCGGCTTCGGCTTTACTAACGTGACCGCACACCAAAAGTGGAAGTTTAGCAGGC

CCGGAATTCGCCTCCTTAGTGTGAAAGCCCAGACCGCTCATATAGTCCTTGAAGACGGC

ACAAAAATGAAAGGCTACTCATTCGGCCATCCATCATCTGTAGCCGGTCAGGTCGTGTT

CAATACTGGATTGGGGGGTTATCCCGAGGCCATAACAGACCCAGCTTATAAGGGCCAGA

TCCTGACCATGGCCAACCCAATCATCGGGAACGGAGGTGCGCCGGATACAACTGCGTTG

GATGAGCTGGGACTGTCCAAGTACTTGGAGAGCAATGGAATTAAAGTTTCTGGACTGCT

GGTACTGGACTACTCAAAGGACTACAATCATTGGCTGGCCACCAAAAGTCTGGGGCAAT

GGCTGCAGGAGGAGAAGGTGCCAGCTATATACGGAGTTGACACTAGAATGCTTACCAAA

ATTATAAGAGACAAAGGTACTATGCTGGGAAAAATTGAGTTTGAAGGACAGCCCGTGGA

TTTCGTAGACCCTAATAAGCAGAATCTTATCGCCGAGGTGAGCACAAAGGACGTTAAGG

TCTACGGAAAAGGAAATCCAACTAAGGTGGTGGCTGTTGATTGTGGCATTAAGAACAAC

GTGATCAGACTGCTGGTGAAACGCGGAGCTGAAGTCCATCTTGTCCCATGGAATCATGA

TTTTACGAAAATGGAGTATGATGGAATTCTCATCGCCGGCGGACCAGGGAACCCAGCCT

TGGCTGAACCCCTTATCCAAAACGTTAGAAAAATACTCGAATCTGATAGGAAAGAGCCC

CTTTTTGGTATATCCACCGGAAACTTGATTACAGGCCTTGCTGCAGGGGCCAAGACATA

TAAGATGAGCATGGCAAACCGCGGACAGAATCAGCCCGTACTGAACATTACTAATAAGC

AGGCTTTTATCACCGCACAGAATCACGGTTACGCTCTCGATAATACGCTCCCTGCCGGC

TGGAAGCCGCTCTTCGTTAACGTAAATGATCAGACAAACGAGGGAATAATGCACGAATC

CAAACCCTTCTTCGCCGTCCAGTTCCACCCTGAAGTCACTCCAGGCCCTATTGACACAG

AATATCTCTTTGACTCCTTCTTTAGCCTGATAAAAAAGGGGAAGGCCACCACCATAACG
```

-continued

```
TCCGTCCTGCCTAAGCCAGCTCTCGTGGCATCAAGAGTAGAGGTCTCCAAAGTGCTCAT
ACTTGGTAGCGGGGGACTGTGAATCGGCCAAGCAGGCGAGTTCGATTACTCCGGAAGCC
AAGCAGTTAAGGCTATGAAAGAAGAGAACGTTAAAACTGTGCTGATGAATCCAAATATA
GCCTCCGTGCAGACCAATGAGGTGGGTCTCAAGCAAGCAGATACTGTTTACTTTCTTCC
AATTACCCCCCAATTCGTAACCGAAGTCATTAAGGCCGAGCAGCCTGATGGATTGATCC
TGGGTATGGGCGGACAGACTGCACTGAATTGCGGAGTGGAGTTGTTCAAAAGGGGTGTG
TTGAAGGAATATGGAGTTAAGGTACTCGGCACCTCCGTTGAGAGCATCATGGCGACCGA
GGATAGACAGTTGTTCTCTGATAAACTGAACGAGATTAATGAGAAGATCGCCCCCTCAT
TCGCCGTGGAGTCTATCGAAGATGCACTGAAAGCCGCTGATACGATTGGCTATCCTGTA
ATGATAAGAAGCGCCTACGCCCTGGGTGGCCTGGGGTCTGGCATCTGCCCTAACCGAGA
GACGCTGATGGACCTCTCCAGAAAAGCCTTCGCCATGACTAACCAGATTCTGGTAGAAA
AATCCGTCACCGGCTGGAAGGAAATTGAATACGAAGTAGTAAGAGACGCTGATGACAAT
TGCGTCACAGTCTGCAACATGGAAAACGTCGATGCGATGGGCGTGCACACCGGAGATTC
CGTCGTTGTGGCGCCAGCACAAACACTCTCCAATGCTGAGTTCCAGATGCTCAGAAGAA
CAAGCATTAACGTTGTGCGACATCTTGGGATAGTTGGCGAATGTAACATCCAATTTGCA
CTGCACCCAACTAGCATGGAATACTGCATTATCGAAGTGAATGCGCGGCTGAGCCGAAG
CAGCGCTCTCGCCAGCAAAGCCACAGGCTACCCACTTGCCTTCATTGCCGCAAAGATTG
CACTGGGCATTCCACTGCCTGAGATTAAGAATGTCGTAAGCGGGAAGACAAGCGCCTGT
TTTGAACCTTCCCTGGACTATATGGTGACTAAGATTCCTCGGTGGGACCTTGATAGGTT
CCATGGGACCTCATCTaGAATAGGATCATCAATGAAGTCTGTGGGTGAAGTGATGGCTA
TCGGGCGGACCTTcGAaGAGAGTTTTCAGAAAGCACTTCGGATGTGTCACCCCTCAATT
GAGGGCTTCACCCCCCGGTTGCCAATGAACAAGGAGTGGCCATCAAACCTGGACCTGAG
AAAAGAGCTCAGCGAGCCTAGCTCAACTAGAATCTACGCAATCGCCAAGGCAATCGACG
ATAACATGTCATTGGATGAGATAGAGAAGTTGACATACATAGACAAATGGTTCCTCTAC
AAAATGCGAGACATTCTGAATATGGAGAAAACACTGAAGGGACTGAATTCTGAGAGCAT
GACGGAGGAGACACTTAAGAGAGCAAAAGAGATTGGGTTCAGCGATAAGCAAATTTCAA
AGTGCCTTGGACTGACCGAAGCCCAGACACGGGAGCTGAGACTGAAGAAAAATATACAC
CCATGGGTGAAGCAGATCGACACCCTGGCGGCCGAATATCCCAGCGTTACTAATTACCT
GTATGTTACATATAACGGCCAAGAGCATGACGTAAATTTTGACGATCATGGAATGATGG
TTTTGGGATGCGGTCCCTACCACATTGGCTCTTCAGTGGAGTTTGATTGGTGCGCAGTG
AGCTCCATTCGGACCCTCAGACAGCTTGGAAAAAAAACAGTGGTGGTAAATTGTAACCC
GGAGACTGTGTCAACCGACTTCGACGAATGCGACAAGTTGTATTTTGAGGAATTGAGTC
TTGAAAGGATTCTTGATATCTACCATCAGGAAGCATGCGGAGGCTGTATTATCTCAGTG
GGCGGGCAGATACCCAACAACCTTGCTGTACCTCTCTATAAAAACGGTGTAAAGATCAT
GGGCACCTCTCCCCTCCAGATTGACAGGGCCGAGGACCGCTCAATTTTCAGTGCTGTGC
TGGACGAACTCAAAGTCGCTCAAGCTCCTTGGAAAGCTGTTAATACTCTTAACGAGGCC
CTcGAgTTCGCCAAGTCTGTGGATTACCCATGTCTTCTTCGGCCCTCCTACGTGCTGTC
AGGaTCcGCAATGAACGTCGTGTTCAGCGAGGATGAAATGAAGAAATTTCTGGAGGAGG
CTACACGGGTGAGTCAAGAGCATCCTGTGGTTTTGACTAAGTTCGTTGAGGGCGCCCGG
GAAGTCGAGATGGATGCAGTCGGTAAAGATGGACGGGTAATTAGCCACGCAATTAGTGA
```

-continued

```
ACACGTGGAAGATGCCGGGGTCCATTCTGGCGACGCCACTCTCATGCTGCCAACACAGA

CAATTAGTCAGGGTGCTATAGAGAAAGTGAAAGATGCGACTAGGAAGATCGCAAAAGCC

TTCGCAATATCTGGCCCATTTAACGTGCAGTTTCTCGTGAAAGGTAACGACGTCCTGGT

GATCGAGTGTAATCTCCGAGCGTCACGATCCTTCCCTTTCGTAAGCAAGACCCTCGGCG

TAGACTTTATTGACGTGGCCACGAAAGTTATGATTGGAGAGAATGTAGACGAGAAACAC

CTCCCCACTCTTGACCATCCGATCATCCCCGCGGATTATGTTGCCATCAAGGCCCCAAT

GTTCTCTTGGCCGCGCCTGCGAGACGCTGATCCCATCTTGCGCTGTGAAATGGCAAGCA

CAGGCGAAGTAGCATGCTTCGGCGAAGGTATTCATACCGCATTTCTGAAGGCCATGCTG

AGCACCGGCTTCAAGATCCCCCAGAAGGGTATCCTCATCGGCATCCAGCAGTCTTTCCG

CCCAAGATTCCTGGGGGTAGCAGAACAACTTCATAACGAAGGCTTCAAGCTGTTTGCAA

CAGAAGCAACCTCTGATTGGCTGAACGCTAATAATGTTCCTGCGACTCCAGTCGCCTGG

CCCAGCCAGGAAGGACAAAATCCCAGCCTGTCTAGCATCAGAAAACTCATACGAGATGG

CTCTATCGACCTTGTTATCAACCTGCCTAATAACAACACCAAATTTGTCCACGACAACT

ACGTCATCAGAAGAACTGCCGTGGATAGCGGTATCCCCCTGCTGACCAATTTCCAGGTT

ACCAAGCTCTTTGCAGAAGCTGTTCAGAAATCTCGCAAGGTGGATAGCAAGTCACTGTT

TCACTATCGACAATATTCAGCGGGGAAGGCTGCATAG
```

SEQ ID NO: 3 below shows an Illustrative Overlapping/Shared hcoCPS1 sequence:

```
                                                     (SEQ ID NO: 3)
GCCGTGGAGTCTATCGAAGATGCACTGAAAGCCGCTGATACGATTGGCTA

TCCTGTAATGATAAGAAGCGCCTACGCCCTGGGTGGCCTGGGGTCTGGCA

TCTGCCCTAACCGAGAGACGCTGATGGACCTCTCCACAAAAGCCTTCGCC

ATGACTAACCAGATTCTGGTAGAAAAATCCGTCACCGGCTGGAAGGAAAT

TGAATACGAAGTAGTAAGAGACGCTGATGACAATTGCGTCACAGTCTGCA

ACATGGAAAACGTCGATGCGATGGGCGTGCACACCGGAGATTCCGTCGTT

GTGGCGCCAGCACAAACACTCTCCAATGCTGAGTTCCAGATGCTCAGAAG

AACAAGCATTAACGTTGTGCGACATCTTGGGATAGTTGGCGAATGTAACA

TCCAATTTGCACTGCACCCAACTAGCATGGAATACTGCATTATCGAAGTG

AATGCGCGGCTGAGCCG
```

SEQ ID NO: 4 below shows an illustrative 5° ITR sequence

```
                                                     (SEQ ID NO: 4)
GCTGCGCGCTCGCTCGCTCACTGAGGCCGCCCGGGCAAAGCCCGGGCGTC

GGGCGACCTTTGGTCGCCCGGCCTCAGTGAGCGAGCGAGCGCGCAGAGAG

GGAGTGGCCAACTCCATCACTAGGGGTTCCTTGTAGTTAATGATTAACCC

GCCATGCTACTTATCTACCAGGGTAATGGG
```

SEQ ID NO: 5 below shows an Illustrative promoter sequence
CAG promoter (CMV enhancer+CBA promoter+BG+chimeric intron)

```
                                                     (SEQ ID NO: 5)
GACATTGATTATTGACTAGTTATTAATAGTAATCAATTACGGGGCATTAG

TTCATAGCCCATATATGGAGTTCCGCGTTACATAACTTACGGTAAATGGC

CCGCCTGGCTGACCGCCCAACGACCCCCGCCCATTGACGTCAATAATGAC

GTATGTTCCCATAGTAACGCCAATAGGGACTTTCCATTGACGTCAATGGG

TGGAGTATTTACGGTAAACTGCCCACTTGGCAGTACATCAAGTGTATCAT

ATGCCAAGTACGCCCCCTATTGACGTCAATGACGGTAAATGGCCCGCCTG

GCATTATGCCCAGTACATGACCTTATGGGACTTTCCTACTTGGCAGTACA

TCTACGTATTAGTCATCGCTATTACCATGGTCGAGGTGAGCCCCACGTTC

TGCTTCACTCTCCCCATCTCCCCCCCCTCCCCACCCCCAATTTTGTATTT

ATTTATTTTTTAATTATTTTGTGCAGCGATGGGGGCGGGGGGGGGGGGGG

GGCGCGCGCCAGGCGGGGCGGGGCGGGGCGAGGGGCGGGGCGGGGCGAGG

CGGAGAGGTGCGGCGGCAGCCAATCAGAGCGGCGCGCTCCGAAAGTTTCC

TTTTATGGCGAGGCGGCGGCGGCGGCGGCCCTATAAAAAGCGAAGCGCGC

GGCGGGCGGGAGTCGCTGCGCGCTGCCTTCGCCCCGTGCCCCGCTCCGCC

GCCGCCTCGCGCCGCCCGCCCCGGCTCTGACTGACCGCGTTACTCCCACA

GGTGAGCGGGCGGGACGGCCCTTCTCCTCCGGGCTGTAATTAGCGCTTGG

TTTAATGACGGCTTGTTTCTTTTCTGTGGCTGCGTGAAAGCCTTGAGGGG

CTCCGGGAGGGCCCTTTGTGCGGGGGGAGCGGCTCGGGGGGTGCGTGCGT

GTGTGTGTGCGTGGGGAGCGCCGCGTGCGGCTCCGCGCTGCCCGGCGGCT

GTGAGCGCTGCGGGCGCGGCGCGGGGCTTTGTGCGCTCCGCAGTGTGCGC

GAGGGGAGCGCGGCCGGGGCGGTGCCCCGCGGTGCGGGGGGGGCTGCGA

GGGGAACAAAGGCTGCGTGCGGGGTGTGTGCGTGGGGGGTGAGCAGGGG

GTGTGGGCGCGTCGGTCGGGCTGCAACCCCCCCTGCACCCCCCTCCCCGA
```

```
GTTGCTGAGCACGGCCCGGCTTCGGGTGCGGGGCTCCGTACGGGGCGTGG

CGCGGGGCTCGCCGTGCCGGGCGGGGGGTGGCGGCAGGTGGGGGTGCCGG

GCGGGGCGGGGCCGCCTCGGGCCGGGGAGGGCTCGGGGAGGGGCGCGGC

GGCCCCCGGAGCGCCGGCGGCTGTCGAGGCGCGGCGAGCCGCAGCCATTG

CCTTTTATGGTAATCGTGCGAGAGGGCGCAGGGACTTCCTTTGTCCCAAA

TCTGTGCGGAGCCGAAATCTGGGAGGCGCCGCCGCACCCCCTCTAGCGGG

CGCGGGGCGAAGCGGTGCGGCGCCGGCAGGAAGGAAATGGGCGGGGAGGG

CCTTCGTGCGTCGCCGCGCCGCCGTCCCCTTCTCCCTCTCCAGCCTCGGG

GCTGTCCGCGGGGGACGGCTGCCTTCGGGGGGGACGGGGCAGGGCGGGG

TTCGGCTTCTGGCGTGTGACCGGCGGCTCTAGAGCCTCTGCTAACCATCT

TCATGCCTTCTTCTTTTTCCTACAG
```

SEQ ID NO: 6 below shows an Illustrative polyA signal sequence

```
                                               (SEQ ID NO: 6)
AATAAAGGAAATTTATTTTCATTGCAATAGTGTGTTGGAATTTTTTGTGT

CTCTCA
```

SEQ ID NO: 7 below shows an illustrative 3' ITR sequence

```
                                               (SEQ ID NO: 7)
CCCATTACCCTGGTAGATAAGTAGCATGGCGGGTTAATCATTAACTACAA

GGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGG

GCGGCCTCAGTGAGCGAGCGAGCGCGCAGC
```

SEQ ID NO: 8 and SEQ ID NO: 9 below show sequences from illustrative working embodiments of a first adeno-associated viral vector comprising a first segment of a codon optimized carbamoyl phosphate synthetase 1 polynucleotide and a second adeno-associated viral vector comprising a second segment of a codon optimized carbamoyl phosphate synthetase 1 polynucleotide. In SEQ ID NO: 8, the underlined sequences are overlapping/shared 5' sequences of the human CPS1 polypeptide. In SEQ ID NO: 9, the underlined sequences are overlapping/shared 3' sequences of the human CPS1 polypeptide.

```
                                               (SEQ ID NO: 8)
GCTGCGCGCTCGCTCGCTCACTGAGGCCGCCCGGGCAAAGCCCGGGCGTCGGGCGACCTT

TGGTCGCCCGGCCTCAGTGAGCGAGCGAGCGCGCAGAGAGGGAGTGGCCAACTCCATCAC

TAGGGGTTCCTTGTAGTTAATGATTAACCCGCCATGCTACTTATCTACCAGGGTAATGGG

GATCCTCTAGAACTATAGCTAGTCGACATTGATTATTGACTAGTTATTAATAGTAATCAA

TTACGGGGTCATTAGTTCATAGCCCATATATGGAGTTCCGCGTTACATAACTTACGGTAA

ATGGCCCGCCTGGCTGACCGCCCAACGACCCCCGCCCATTGACGTCAATAATGACGTATG

TTCCCATAGTAACGCCAATAGGGACTTTCCATTGACGTCAATGGGTGGAGTATTTACGGT

AAACTGCCCACTTGGCAGTACATCAAGTGTATCATATGCCAAGTACGCCCCCTATTGACG

TCAATGACGGTAAATGGCCCGCCTGGCATTATGCCCAGTACATGACCTTATGGGACTTTC

CTACTTGGCAGTACATCTACGTATTAGTCATCGCTATTACCATGGTCGAGGTGAGCCCCA

CGTTCTGCTTCACTCTCCCCATCTCCCCCCCCTCCCCACCCCCAATTTTGTATTTATTTA

TTTTTTAATTATTTTGTGCAGCGATGGGGGCGGGGGGGGGGGGGGCGCGCGCCAGGCG

GGGCGGGGCGGGGCGAGGGGCGGGGCGGGCGAGGCGGAGAGGTGCGGCGGCAGCCAATC

AGAGCGGCGCGCTCCGAAAGTTTCCTTTTATGGCGAGGCGGCGGCGGCGGCGGCCCTATA

AAAAGCGAAGCGCGCGGCGGGCGGGAGTCGCTGCGCGCTGCCTTCGCCCCGTGCCCCGCT

CCGCCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTTG

TTTCTTTTCTGTGGCTGCGTGAAAGCCTTGAGGGGCTCCGGGAGGGCCCTTTGTGCGGGG

GGAGCGGCTCGGGGGGTGCGTGCGTGTGTGTGCGTGGGGAGCGCCGCGTGCGGCTCCG

CGCTGCCCGGCGGCTGTGAGCGCTGCGGGCGCGGCGCGGGCTTTGTGCGCTCCGCAGTG

TGCGCGAGGGGAGCGCGGCCGGGGCGGTGCCCCGCGGTGCGGGGGGGCTGCGAGGGGA

ACAAAGGCTGCGTGCGGGGTGTGTGCGTGGGGGGGTGAGCAGGGGGTGTGGGCGCGTCGG

TCGGGCTGCAACCCCCCCTGCACCCCCCTCCCCGAGTTGCTGAGCACGGCCCGGCTTCGG

GTGCGGGGCTCCGTACGGGGCGTGGCGCGGGGCTCGCCGTGCCGGGCGGGGGTGGCGGC
```

-continued

```
AGGTGGGGGTGCCGGGCGGGGCGGGGCCGCCTCGGGCCGGGGAGGGCTCGGGGGAGGGGC
GCGGCGGCCCCCGGAGCGCCGGCGGCTGTCGAGGCGCGGCGAGCCGCAGCCATTGCCTTT
TATGGTAATCGTGCGAGAGGGCGCAGGGACTTCCTTTGTCCCAAATCTGTGCGGAGCCGA
AATCTGGGAGGCGCCGCCGCACCCCCTCTAGCGGGCGCGGGGCGAAGCGGTGCGGCGCCG
GCAGGAAGGAAATGGGCGGGGAGGGCCTTCGTGCGTCGCCGCGCCGCCGTCCCCTTCTCC
CTCTCCAGCCTCGGGGCTGTCCGCGGGGGGACGGCTGCCTTCGGGGGGGACGGGGCAGGG
CGGGGTTCGGCTTCTGGCGTGTGACCGGCGGCTCTAGAGCCTCTGCTAACCATGTTCATG
CCTTCTTCTTTTTCCTACAGCTCCTGGGCAACGTGCTGGTTATTGTGCTGTCTCATCATT
TTGGCAAAGAATTCACGCGTGGTACCACTAGTCATATGTTAATTAAATGCCTCAGATCAT
AAAGATGACCCGGATTCTTACCGCATTCAAGGTTGTAAGGACCCTTAAAACCGGCTTCGG
CTTTACTAACGTGACCGCACACCAAAAGTGGAAGTTTAGCAGGCCCGGAATTCGCCTCCT
TAGTGTGAAAGCCCAGACCGCTCATATAGTCCTTGAAGACGGCACAAAAATGAAAGGGTA
CTCATTCGGCCATCCATCATCTGTAGCCGGTGAGGTCGTGTTCAATACTGGATTGGGGGG
TTATCCCGAGGCCATAACAGACCCAGCTTATAAGGGCCAGATCCTGACCATGGCCAACCC
AATCATCGGGAACGGAGGTGCGCCGGATACAACTGCGTTGGATGAGCTGGGACTGTCCAA
GTACTTGGAGAGCAATGGAATTAAAGTTTCTGGACTGCTGGTACTGGACTACTCAAAGGA
CTACAATCATTGGCTGGCCACCAAAAGTCTGGGGCAATGGCTGCAGGAGGAGAAGGTGCC
AGCTATATACGGAGTTGACACTAGAATGCTTACCAAAATTATAAGAGACAAAGGTACTAT
GCTGGGAAAAATTGAGTTTGAAGGACAGCCCGTGGATTTCGTAGACCCTAATAAGCAGAA
TCTTATCGCCGAGGTGAGCACAAAGGACGTTAAGGTCTACGGAAAAGGAAATCCAACTAA
GGTGGTGGCTGTTGATTGTGGCATTAAGAACAACGTGATCAGACTGCTGGTGAAACGCGG
AGCTGAAGTCCATCTTGTCCCATGGAATCATGATTTTACGAAAATGGAGTATGATGGAAT
TCTCATCGCCGGCGGACCAGGGAACCCAGCCTTGGCTGAACCCCTTATCCAAAACGTTAG
AAAAATACTCGAATCTGATAGGAAAGAGCCCCTTTTTGGTATATCCACCGGAAACTTGAT
TACAGGCCTTGCTGCAGGGGCCAAGACATATAAGATGAGCATGGCAAACCGCGGACAGAA
TCAGCCCGTACTGAACATTACTAATAAGCAGGCTTTTATCACCGCACAGAATCACGGTTA
CGCTCTCGATAATACGCTCCCTGCCGGCTGGAAGCCGCTCTTCGTTAACGTAAATGATCA
GACAAACGAGGGAATAATGCACGAATCCAAACCCTTCTTCGCCGTCCAGTTCCACCCTGA
AGTCACTCCAGGCCCTATTGACACAGAATATCTCTTTGACTCCTTCTTTAGCCTGATAAA
AAAGGGGAAGGCCACCACCATAACGTCCGTCCTGCCTAAGCCAGCTCTCGTGGCATCAAG
AGTAGAGGTCTCCAAAGTGCTCATACTTGGTAGCGGGGACTGTCAATCGGCCAAGCAGG
CGAGTTCGATTACTCCGGAAGCCAAGCAGTTAAGGCTATGAAAGAAGAGAACGTTAAAAC
TGTGCTGATGAATCCAAATATAGCCTCCGTGCAGACCAATGAGGTGGGTCTCAAGCAAGC
AGATACTGTTTACTTTCTTCCAATTACCCCCCAATTCGTAACCGAAGTCATTAAGGCCGA
GCAGCCTGATGGATTGATCCTGGGTATGGGCGGACAGACTGCACTGAATTGCGGAGTGGA
GTTGTTCAAAAGGGGTGTGTTGAAGGAATATGGAGTTAAGGTACTCGGCACCTCCGTTGA
GAGCATCATGGCGACCGAGGATAGACAGTTGTTCTCTGATAAACTGAACGAGATTAATGA
GAAGATCGCCCCCTCATTCGCCGTGGAGTCTATCGAAGATGCACTGAAAGCCGCTGATAC
GATTGGCTATCCTGTAATGATAAGAAGCGCCTACGCCCTGGGTGGCCTGGGGTCTGGCAT
CTGCCCTAACCGAGAGACGCTGATGGACCTCTCCACAAAAGCCTTCGCCATGACTAACCA
GATTCTGGTAGAAAAATCCGTCACCGGCTGGAAGGAAATTGAATACGAAGTAGTAAGAGA
```

-continued

CGCTGATGACAATTGCGTCACAGTCTGCAACATGGAAAACGTCGATGCGATGGGCGTGCA

CACCGGAGATTCCGTCGTTGTGGCGCCAGCACAAACACTCTCCAATGCTGAGTTCGAGAT

GCTCAGAAGAACAAGCATTAACGTTGTGCGACATCTTGGGATAGTTGGCGAATGTAACAT

CCAATTTGCACTGCACCCAACTAGCATGGAATACTGCATTATCGAAGTGAATGCGCGGCT

GAGCCGTCGAGGACGGGGTGAACTACGCCTGAGGATCCGATCTTTTTCCCTCTGCCAAAA

ATTATGGGGACATCATGAAGCCCCTTGAGCATCTGACTTCTGGCTAATAAAGGAAATTTA

TTTTCATTGCAATAGTGTGTTGGAATTTTTTGTGTCTCTCACTCGGAAGCAATTCGTTGA

TCTGAATTTCGACCACCCATAATACCCATTACCCTGGTAGATAAGTAGCATGGCGGGTTA

ATCATTAACTACAAGGAACCCCTAGTGATGGAGTTGGCCACTCCCTCTCTGCGCGCTCGC

TCGCTCACTGAGGCCGGGCGACCAAAGGTCGCCCGACGCCCGGGCTTTGCCCGGGCGGCC

TCAGTGAGCGAGCGAGCGCGCAGCCTTAATTAACCTAATTCACTGGCCGTCGTTTTACAA

CGTCGTGACTGGGAAAACCCTGGCGTTACCCAACTTAATCGCCTTGCAGCACATCCCCCT

TTCGCCAGCTGGCGTAATAGCGAAGAGGCCCGCACCGATCGCCCTTCCCAACAGTTGCGC

AGCCTGAATGGCGAATGGGACGCGCCCTGTAGCGGCGCATTAAGCGCGGCGGGTGTGGTG

GTTACGCGCAGCGTGACCGCTACACTTGCCAGCGCCCTAGCGCCCGCTCCTTTCGCTTTC

TTCCCTTCCTTTCTCGCCACGTTCGCCGGCTTTCCCCGTCAAGCTCTAAATCGGGGGCTC

CCTTTAGGGTTCCGATTTAGTGCTTTACGGCACCTCGACCCCAAAAAACTTGATTAGGGT

GATGGTTCACGTAGTGGGCCATCGCCCTGATAGACGGTTTTTCGCCCTTTGACGTTGGAG

TCCACGTTCTTTAATAGTGGACTCTTGTTCCAAACTGGAACAACACTCAACCCTATCTCG

GTCTATTCTTTTGATTTATAAGGGATTTTGCCGATTTCGGCCTATTGGTTAAAAAATGAG

CTGATTTAACAAAAATTTAACGCGAATTTTAACAAAATATTAACGCTTACAATTTAGGTG

GCACTTTTCGGGGAAATGTGCGCGGAACCCCTATTTGTTTATTTTTCTAAATACATTCAA

ATATGTATCCGCTCATGAGACAATAACCCTGATAAATGCTTCAATAATATTGAAAAAGGA

AGAGTATGAGTATTCAACATTTCCGTGTCGCCCTTATTCCCTTTTTTGCGGCATTTTGCC

TTCCTGTTTTTGCTCACCCAGAAACGCTGGTGAAAGTAAAAGATGCTGAAGATCAGTTGG

GTGCACGAGTGGGTTACATCGAACTGGATCTCAACAGCGGTAAGATCCTTGAGAGTTTTC

GCCCCGAAGAACGTTTTCCAATGATGAGCACTTTTAAAGTTCTGCTATGTGGCGCGGTAT

TATCCCGTATTGACGCCGGGCAAGAGCAACTCGGTCGCCGCATACACTATTCTCAGAATG

ACTTGGTTGAGTACTCACCAGTCACAGAAAAGCATCTTACGGATGGCATGACAGTAAGAG

AATTATGCAGTGCTGCCATAACCATGAGTGATAACACTGCGGCCAACTTACTTCTGACAA

CGATCGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGACACCA

CGATGCCTGTAGCAATGGCAACAACGTTGCGCAAACTATTAACTGGCGAACTACTTACTC

TAGCTTCCCGGCAACAATTAATAGACTGGATGGAGGCGGATAAAGTTGCAGGACCACTTC

TGCGCTCGGCCCTTCCGGCTGGCTGGTTTATTGCTGATAAATCTGGAGCCGGTGAGCGTG

GGTCTCGCGGTATCATTGCAGCACTGGGGCCAGATGGTAAGCCCTCCCGTATCGTAGTTA

TCTACACGACGGGGAGTCAGGCAACTATGGATGAACGAAATAGACAGATCGCTGAGATAG

GTGCCTCACTGATTAAGCATTGGTAACTGTCAGACCAAGTTTACTCATATATACTTTAGA

TTGATTTAAAACTTCATTTTTAATTTAAAAGGATCTAGGTGAAGATCCTTTTTGATAATC

TCATGACCAAAATCCCTTAACGTGAGTTTTCGTTCCACTGAGCGTCAGACCCCGTAGAAA

```
AGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTC

CGAAGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAATCC

TGTTACCAGTGGCTGCTGCCAGTGGCGATAAGTCGTGTCTTACCGGGTTGGACTCAAGAC

GATAGTTACCGGATAAGGCGCAGCGGTCGGGCTGAACGGGGGGTTCGTGCACACAGCCCA

GCTTGGAGCGAACGACCTACACCGAACTGAGATACCTACAGCGTGAGCTATGAGAAAGCG

CCACGCTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTCGGGT

TTCGCCACCTCTGACTTGAGCGTCGATTTTTGTGATGCTCGTCAGGGGGCGGAGCCTAT

GGAAAAACGCCAGCAACGCGGCCTTTTTACGGTTCCTGGCCTTTTGCTGGCCTTTTGCTC

ACATGTTCTTTCCTGCGTTATCCCCTGATTCTGTGGATAACCGTATTAGCGCCTTTGAGT

GAGCTGATACCGCTCGCCGCAGCCGAACGACCGAGCGCAGCGAGTCAGTGAGCGAGGAAG

CGGAAGAGCGCCCAATACGCAAACCGCCTCTCCCCGCGCGTTGGCCGATTCATTAATGCA

GCTGGCACGACAGGTTTCCCGACTGGAAAGCGGGCAGTGAGCGCAACGCAATTAATGTGA

GTTAGCTCACTCATTAGGCACCCCAGGCTTTACACTTTATGCTTCCGGCTCGTATGTTGT

GTGGAATTGTGAGCGGATAACAATTTCACACAGGAAACAGCTATGACCATGATTACGCCA

GATTTAATTAAGGCCTTAATTAG (SEQ ID NO: 9)
GCTGCGCGCTCGCTCGCTCACTGAGGCCGCCCGGGCAAAGCCCGGGCGTCGGGCGACCTT

TGGTCGCCCGGCCTCAGTGAGCGAGCGAGCGCGCAGAGAGGGAGTGGCCAACTCCATCAC

TAGGGGTTCCTTGTAGTTAATGATTAACCCGCCATGCTACTTATCTACCAGGGTAATGGG

GATCTGCCGTGGAGTCTATCGAAGATGCACTGAAAGCCGCTGATACGATTGGCTATCCTG

TAATGATAAGAAGCGCCTACGCCCTGGGTGGCCTGGGGTCTGGCATCTGCCCTAACCGAG

AGACGCTGATGGACCTCTCCACAAAAGCCTTCGCCATGACTAACCAGATTCTGGTAGAAA

AATCCGTCACCGGCTGGAAGGAAATTGAATACGAAGTAGTAAGAGACGCTGATGACAATT

GCGTCACAGTCTGCAACATGGAAAACGTCGATGCGATGGGCGTGCACACCGGAGATTCCG

TCGTTGTGGCGCCAGCACAAACACTCTCCAATGCTGAGTTCCAGATGCTCAGAAGAACAA

GCATTAACGTTGTGCGACATCTTGGGATAGTTGGCGAATGTAACATCCAATTTGCACTGC

ACCCAACTAGCATGGAATACTGCATTATCGAAGTGAATGCGCGGCTGAGCCGAAGCAGCG

CTCTCGCCAGCAAAGCCACAGGCTACCCACTTGCCTTCATTGCCGCAAAGATTGCACTGG

GCATTCCACTGCCTGAGATTAAGAATGTCGTAAGCGGGAAGACAAGCGCCTGTTTTGAAC

CTTCCCTGGACTATATGGTGACTAAGATTCCTCGGTGGGACCTTGATAGGTTCCATGGGA

CCTCATCTAGAATAGGATCATCAATGAAGTCTGTGGGTGAAGTGATGGCTATCGGGCGGA

CCTTCGAAGAGAGTTTTCAGAAAGCACTTCGGATGTGTCACCCCTCAATTGAGGGCTTCA

CCCCCCGGTTGCCAATGAACAAGGAGTGGCCATCAAACCTGGACCTGAGAAAAGAGCTCA

GCGAGCCTAGCTCAACTAGAATCTACGCAATCGCCAAGGCAATCGACGATAACATGTCAT

TGGATGAGATAGAGAAGTTGACATACATAGACAAATGGTTCCTCTACAAAATGCGAGACA

TTCTGAATATGGAGAAAACACTGAAGGGACTGAATTCTGAGAGCATGACGGAGGAGACAC

TTAAGAGCAAAAGAGATTGGGTTCAGCGATAAGCAAATTTCAAAGTGCCTTGGACTGA

CCGAAGCCCAGACACGGGAGCTGAGACTGAAGAAAAATATACACCCATGGGTGAAGCAGA
```

-continued

```
TCGACACCCTGGCGGCCGAATATCCCAGCGTTACTAATTACCTGTATGTTACATATAACG
GCCAAGAGCATGACGTAAATTTTGACGATCATGGAATGATGGTTTTGGGATGCGGTCCCT
ACCACATTGGCTCTTCAGTGGAGTTTGATTGGTGCGCAGTGAGCTCCATTCGGACCCTCA
GACAGCTTGGAAAAAAAACAGTGGTGGTAAATTGTAACCCGGAGACTGTGTCAACCGACT
TCGACGAATGCGACAAGTTGTATTTTGAGGAATTGAGTCTTGAAAGGATTCTTGATATCT
ACCATCAGGAAGCATGCGGAGGCTGTATTATCTCAGTGGGCGGGCAGATACCCAACAACC
TTGCTGTACCTCTCTATAAAAACGGTGTAAAGATCATGGGCACCTCTCCCCTCCAGATTG
ACAGGGCCGAGGACCGCTCAATTTTCAGTGCTGTGCTGGACGAACTCAAAGTCGCTCAAG
CTCCTTGGAAAGCTGTTAATACTCTTAACGAGGCCCTCGAGTTCGCCAAGTCTGTGGATT
ACCCATGTCTTCTTCGGCCCTCCTACGTGCTGTCAGGATCCGCAATGAACGTCGTGTTCA
GCGAGGATGAAATGAAGAAATTTCTGGAGGAGGCTACACGGGTGAGTCAAGAGCATCCTG
TGGTTTTGACTAAGTTCGTTGAGGGCGCCCGGGAAGTCGAGATGGATGCAGTCGGTAAAG
ATGGACGGGTAATTAGCCACGCAATTAGTGAACACGTGGAAGATGCCGGGGTCCATTCTG
GCGACGCCACTCTCATGCTGCCAACACAGACAATTAGTCAGGGTGCTATAGAGAAAGTGA
AAGATGCGACTAGGAAGATCGCAAAAGCCTTCGCAATATCTGGCCCATTTAACGTGCAGT
TTCTCGTGAAAGGTAACGACGTCCTGGTGATCGAGTGTAATCTCCGAGCGTCACGATCCT
TCCCTTTCGTAAGCAAGACCCTCGGCGTAGACTTTATTGACGTGGCCACGAAAGTTATGA
TTGGAGAGAATGTAGACGAGAAACACCTCCCCACTCTTGACCATCCGATCATCCCCGCGG
ATTATGTTGCCATCAAGGCCCGAATGTTCTCTTGGCCGCGCCTGCGAGACGCTGATCCCA
TCTTGCGCTGTGAAATGGCAAGCACAGGCGAAGTAGCATGCTTCGGCGAAGGTATTCATA
CCGCATTTCTGAAGGCCATGCTGAGCACCGGCTTCAAGATCCCCCAGAAGGGTATCCTCA
TCGGCATCCAGCAGTCTTTCCGCCCAAGATTCCTGGGGGTAGCAGAACAACTTCATAACG
AAGGCTTCAAGCTGTTTGCAACAGAAGCAACCTCTGATTGGCTGAACGCTAATAATGTTC
CTGCGACTCCAGTCGCCTGGCCCAGCCAGGAAGGACAAAATCCCAGCCTGTCTAGCATCA
GAAAACTCATACGAGATGGCTCTATCGACCTTGTTATCAACCTGCCTAATAACAACACCA
AATTTGTCCACGACAACTACGTCATCAGAAGAACTGCCGTGGATAGCGGTATCCCCCTGC
TGACCAATTTCCAGGTTACCAAGCTCTTTGCAGAAGCTGTTCAGAAATCTCGCAAGGTGG
ATAGCAAGTCACTGTTTCACTATCGACAATATTCAGCGGGAAGGCTGCATAGGCGGCCG
CACCGGTAAGCTTGGTACCACTAGTCATATGTTAATTAAGTCGACAGATCCGATCTTTTT
CCCTCTGCCAAAAATTATGGGGACATCATGAAGCCCCTTGAGCATCTGACTTCTGGCTAA
TAAAGGAAATTTATTTTCATTGCAATAGTGTGTTGGAATTTTTTGTGTCTCTCACTCGGA
AGCAATTCGTTGATCTGAATTTCGACCACCCATAATACCCATTACCCTGGTAGATAAGTA
GCATGGCGGGTTAATCATTAACTACAAGGAACCCCTAGTGATGGAGTTGGCCACTCCCTC
TCTGCGCGCTCGCTCGCTCACTGAGGCCGGGCGACCAAAGGTCGCCCGACGCCCGGGCTT
TGCCCGGGCGGCCTCAGTGAGCGAGCGAGCGCGCAGCCTTAATTAACCTAATTCACTGGC
CGTCGTTTTACAACGTCGTGACTGGGAAAACCCTGGCGTTACCCAACTTAATCGCCTTGC
AGCACATCCCCCTTTCGCCAGCTGGCGTAATAGCGAAGAGGCCCGCACCGATCGCCCTTC
CCAACAGTTGCGCAGCCTGAATGGCGAATGGGACGCGCCCTGTAGCGGCGCATTAAGCGC
GGCGGGTGTGGTGGTTACGCGCAGCGTGACCGCTACACTTGCCAGCGCCCTAGCGCCCGC
TCCTTTCGCTTTCTTCCCTTCCTTTCTCGCCACGTTCGCCGGCTTTCCCCGTCAAGCTCT
AAATCGGGGGCTCCCTTTAGGGTTCCGATTTAGTGCTTTACGGCACCTCGACCCCAAAAA
```

-continued

```
ACTTGATTAGGGTGATGGTTCACGTAGTGGGCCATCGCCCTGATAGACGGTTTTTCGCCC

TTTGACGTTGGAGTCCACGTTCTTTAATAGTGGACTCTTGTTCCAAACTGGAACAACACT

CAACCCTATCTCGGTCTATTCTTTTGATTTATAAGGGATTTTGCCGATTTCGGCCTATTG

GTTAAAAAATGAGCTGATTTAACAAAAATTTAACGCGAATTTTAACAAAATATTAACGCT

TACAATTTAGGTGGCACTTTTCGGGGAAATGTGCGCGGAACCCCTATTTGTTTATTTTTC

TAAATACATTCAAATATGTATCCGCTCATGAGACAATAACCCTGATAAATGCTTCAATAA

TATTGAAAAAGGAAGAGTATGAGTATTCAACATTTCCGTGTCGCCCTTATTCCCTTTTTT

GCGGCATTTTGCCTTCCTGTTTTTGCTCACCCAGAAACGCTGGTGAAAGTAAAAGATGCT

GAAGATCAGTTGGGTGCACGAGTGGGTTACATCGAACTGGATCTCAACAGCGGTAAGATC

CTTGAGAGTTTTCGCCCCGAAGAACGTTTTCCAATGATGAGCACTTTTAAAGTTCTGCTA

TGTGGCGCGGTATTATCCCGTATTGACGCCGGGCAAGAGCAACTCGGTCGCCGCATACAC

TATTCTCAGAATGACTTGGTTGAGTACTCACCAGTCACAGAAAAGCATCTTACGGATGGC

ATGACAGTAAGAGAATTATGCAGTGCTGCCATAACCATGAGTGATAACACTGCGGCCAAC

TTACTTCTGACAACGATCGGAGGACCGAAGGAGCTAACCGCTTTTTTGCACAACATGGGG

GATCATGTAACTCGCCTTGATCGTTGGGAACCGGAGCTGAATGAAGCCATACCAAACGAC

GAGCGTGACACCACGATGCCTGTAGCAATGGCAACAACGTTGCGCAAACTATTAACTGGC

GAACTACTTACTCTAGCTTCCCGGCAACAATTAATAGACTGGATGGAGGCGGATAAAGTT

GCAGGACCACTTCTGCGCTCGGCCCTTCCGGCTGGCTGGTTTATTGCTGATAAATCTGGA

GCCGGTGAGCGTGGGTCTCGCGGTATCATTGCAGCACTGGGGCCAGATGGTAAGCCCTCC

CGTATCGTAGTTATCTACACGACGGGGAGTCAGGCAACTATGGATGAACGAAATAGACAG

ATCGCTGAGATAGGTGCCTCACTGATTAAGCATTGGTAACTGTCAGACCAAGTTTACTCA

TATATACTTTAGATTGATTTAAAACTTCATTTTTAATTTAAAAGGATCTAGGTGAAGATC

CTTTTTGATAATCTCATGACCAAAATCCCTTAACGTGAGTTTTCGTTCCACTGAGCGTCA

GACCCCGTAGAAAAGATCAAAGGATCTTCTTGAGATCCTTTTTTTCTGCGCGTAATCTGC

TGCTTGCAAACAAAAAAACCACCGCTACCAGCGGTGGTTTGTTTGCCGGATCAAGAGCTA

CCAACTCTTTTTCCGAAGGTAACTGGCTTCAGCAGAGCGCAGATACCAAATACTGTTCTT

CTAGTGTAGCCGTAGTTAGGCCACCACTTCAAGAACTCTGTAGCACCGCCTACATACCTC

GCTCTGCTAATCCTGTTACCAGTGGCTGCTGCCAGTGGCGATAAGTCGTGTCTTACCGGG

TTGGACTCAAGACGATAGTTACCGGATAAGGCGCAGCGGTCGGGCTGAACGGGGGGTTCG

TGCACACAGCCCAGCTTGGAGCGAACGACCTACACCGAACTGAGATACCTACAGCGTGAG

CTATGAGAAAGCGCCACGCTTCCCGAAGGGAGAAAGGCGGACAGGTATCCGGTAAGCGGC

AGGGTCGGAACAGGAGAGCGCACGAGGGAGCTTCCAGGGGGAAACGCCTGGTATCTTTAT

AGTCCTGTCGGGTTTCGCCACCTCTGACTTGAGCGTCGATTTTTGTGATGCTCGTCAGGG

GGGCGGAGCCTATGGAAAAACGCCAGCAACGCGGCCTTTTTACGGTTCCTGGCCTTTTGC

TGGCCTTTTGCTCACATGTTCTTTCCTGCGTTATCCCCTGATTCTGTGGATAACCGTATT

ACCGCCTTTGAGTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCGCGCGTTGGCCG

ATTCATTAATGCAGCTGGCACGACAGGTTTCCCGACTGGAAAGCGGGCAGTGAGCGCAAC
```

-continued

```
GCAATTAATGTGAGTTAGCTCACTCATTAGGCACCCCAGGCTTTACACTTTATGCTTCCG

GCTCGTATGTTGTGTGGAATTGTGAGCGGATAACAATTTCACACAGGAAACAGCTATGAC

CATGATTACGCCAGATTTAATTAAGGCCTTAATTAG
```

CONCLUSION

This concludes the description of embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

---

The invention claimed is:

1. A method of making a pharmaceutical composition comprising combining together in an aqueous formulation:
at least one adeno-associated viral vector comprising a carbamoyl phosphate synthetase 1 polynucleotide sequence (SEQ ID NO: 2); and
a pharmaceutical excipient selected from the group consisting of:
a preservative, a tonicity adjusting agent, a detergent, a viscosity adjusting agent, a sugar or a pH adjusting agent, wherein:
the vector and the carbamoyl phosphate synthetase 1 polynucleotide sequence are selected such that when the adeno-associated viral vector infects a human liver cell, carbamoyl phosphate synthetase 1 protein is expressed;
the method combines two adeno-associated viral vectors comprising:
a first adeno-associated viral vector comprising a first segment of a codon optimized carbamoyl phosphate synthetase 1 polynucleotide (SEQ ID NO: 2); and
a second adeno-associated viral vector comprising a second segment of a codon optimized carbamoyl phosphate synthetase 1 polynucleotide (SEQ ID NO: 2); wherein:
the first adeno-associated viral vector comprising the first segment of a codon optimized carbamoyl phosphate synthetase 1 polynucleotide and the second adeno-associated viral vector comprising the second segment of a codon optimized carbamoyl phosphate synthetase 1 polynucleotide are selected so that:
the first and second segments of the carbamoyl phosphate synthetase 1 polynucleotides overlap such that, following first and second adeno-associated viral vector infection of the human liver cell, the carbamoyl phosphate synthetase 1 polynucleotides concatemerize via homologous recombination so as to reconstitute a carbamoyl phosphate synthetase 1 gene that expresses the carbamoyl phosphate synthetase 1 protein in the liver cell; and
the first segment of the carbamoyl phosphate synthetase 1 polynucleotide is selected to comprise the sequence ATGCCTCAGA.

2. A pharmaceutical composition comprising:
a first adeno-associated viral vector comprising:
(a) a polynucleotide sequence comprising a terminal repeat sequence;
(b) a polynucleotide sequence comprising a promoter;
(c) a codon optimized polynucleotide sequence (SEQ ID NO: 2) comprising a segment of a gene encoding a carbamoyl phosphate synthetase 1 protein; and
(d) a polynucleotide sequence comprising a polyA tail signal; and
a pharmaceutical excipient selected from the group consisting of:
a preservative, a tonicity adjusting agent, a detergent, a viscosity adjusting agent, a sugar or a pH adjusting agent; and
a second adeno-associated viral vector comprising:
(a) a polynucleotide sequence comprising an inverted terminal repeat;
(b) a polynucleotide sequence comprising a promoter; and
(c) a codon optimized polynucleotide sequence comprising a segment of a gene encoding a carbamoyl phosphate synthetase 1 protein; wherein:
the first and second segments of the carbamoyl phosphate synthetase 1 polynucleotides overlap so that, following adeno-associated viral vector infection of a human liver cell, the carbamoyl phosphate synthetase 1 polynucleotides concatemerize via homologous recombination so as to reconstitute a carbamoyl phosphate synthetase 1 polynucleotide that expresses the carbamoyl phosphate synthetase 1 protein in the liver cell; and
the first segment of the carbamoyl phosphate synthetase 1 polynucleotide is selected to comprise the sequence ATGCCTCAGA and the second segment of the carbamoyl phosphate synthetase 1 polynucleotide is selected to comprise the sequence TGCCGTGGAG.

3. The pharmaceutical composition of claim 2, wherein the first and/or the second adeno-associated viral vector further comprises:
a polynucleotide sequence comprising an enhancer;
a polynucleotide sequence comprising a chimeric intron; and/or
a polynucleotide sequence comprising a polyA signal.

4. The pharmaceutical composition of claim 2, wherein the first segment of the carbamoyl phosphate synthetase 1 polynucleotide and the second segment of the carbamoyl phosphate synthetase 1 polynucleotide comprise at least 100 overlapping nucleotides of the carbamoyl phosphate synthetase 1 gene (SEQ ID NO: 2).

5. The pharmaceutical composition of claim 2, wherein the composition comprises an adeno-associated viral vector comprising one or more carbamoyl phosphate synthetase 1 polynucleotide sequences which, when transduced into a human liver cell expresses the carbamoyl phosphate synthetase 1 protein.

6. A method of delivering carbamoyl phosphate synthetase 1 polynucleotides into human cells comprising:
contacting a composition of claim 5 with the human cells so that adeno associated vector(s) infect the cells, thereby delivering the polynucleotides into the cells.

7. The method of claim 6, wherein the composition comprises the first adeno-associated viral vector and the second adeno-associated viral vector.

8. The method of claim 7, wherein the first segment of the carbamoyl phosphate synthetase 1 polynucleotide in the first adeno-associated vector and the second segment of the carbamoyl phosphate synthetase 1 polynucleotide in the second adeno-associated vector comprise at least 100, 200, 300, 400 or 500 overlapping/complementary nucleotides of the carbamoyl phosphate synthetase 1 gene (SEQ ID NO: 2).

9. The method of claim 8, wherein the cells are in vivo liver cells.

10. The method of claim 9, wherein the in vivo liver cells are present in a mammal diagnosed with a carbamoyl phosphate synthetase I deficiency.

11. A method of making a pharmaceutical composition comprising combining together in an aqueous formulation:
at least one adeno-associated viral vector comprising a carbamoyl phosphate synthetase 1 polynucleotide sequence (SEQ ID NO: 2); and
a pharmaceutical excipient selected from the group consisting of:
a preservative, a tonicity adjusting agent, a detergent, a viscosity adjusting agent, a sugar or a pH adjusting agent, wherein:
the vector and the carbamoyl phosphate synthetase 1 polynucleotide sequence are selected such that when the adeno-associated viral vector infects a human liver cell, carbamoyl phosphate synthetase 1 protein is expressed;
the method combines two adeno-associated viral vectors comprising:
a first adeno-associated viral vector comprising a first segment of a codon optimized carbamoyl phosphate synthetase 1 polynucleotide (SEQ ID NO: 2); and
a second adeno-associated viral vector comprising a second segment of a codon optimized carbamoyl phosphate synthetase 1 polynucleotide (SEQ ID NO: 2);
wherein:
the first adeno-associated viral vector comprising the first segment of a codon optimized carbamoyl phosphate synthetase 1 polynucleotide and the second adeno-associated viral vector comprising the second segment of a codon optimized carbamoyl phosphate synthetase 1 polynucleotide are selected so that:
the first and second segments of the carbamoyl phosphate synthetase 1 polynucleotides overlap such that, following first and second adeno-associated viral vector infection of the human liver cell, the carbamoyl phosphate synthetase 1 polynucleotides concatemerize via homologous recombination so as to reconstitute a carbamoyl phosphate synthetase 1 gene that expresses the carbamoyl phosphate synthetase 1 protein in the liver cell; and
wherein the second segment of the carbamoyl phosphate synthetase 1 polynucleotide is selected to comprise the sequence TGCCGTGGAG.

* * * * *